(12) United States Patent
Weisbart et al.

(10) Patent No.: US 12,116,416 B2
(45) Date of Patent: *Oct. 15, 2024

(54) TARGETING INTRACELLULAR TARGET-BINDING DETERMINANTS WITH INTRACELLULAR ANTIBODIES

(71) Applicant: The United States Government As Represented By The Department Of Veterans Affairs, Washington, DC (US)

(72) Inventors: Richard H. Weisbart, Sepulveda, CA (US); Robert N. Nishimura, Sepulveda, CA (US)

(73) Assignee: THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,643

(22) Filed: Oct. 6, 2023

(65) Prior Publication Data

US 2024/0026026 A1 Jan. 25, 2024

Related U.S. Application Data

(60) Continuation of application No. 18/322,846, filed on May 24, 2023, which is a continuation of application No. 16/902,173, filed on Jun. 15, 2020, which is a continuation of application No. 15/042,106, filed on Feb. 11, 2016, now Pat. No. 10,683,363, which is a division of application No. 13/844,318, filed on Mar. 15, 2013, now Pat. No. 9,283,272.

(60) Provisional application No. 61/618,613, filed on Mar. 30, 2012.

(51) Int. Cl.
| | | |
|---|---|---|
| C07K 16/30 | (2006.01) | |
| A61K 39/00 | (2006.01) | |
| A61P 35/00 | (2006.01) | |

(52) U.S. Cl.
CPC .......... C07K 16/3053 (2013.01); A61P 35/00 (2018.01); *A61K 2039/505* (2013.01); *C07K 2317/31* (2013.01); *C07K 2317/622* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs et al. |
| 3,817,837 A | 6/1974 | Rubenstein et al. |
| 3,897,212 A | 7/1975 | Leon et al. |
| 4,134,792 A | 1/1979 | Boguslaski et al. |
| 4,174,384 A | 11/1979 | Ullman et al. |
| 4,220,722 A | 9/1980 | Rowley et al. |
| 4,275,149 A | 6/1981 | Litman et al. |
| 4,299,916 A | 11/1981 | Litman et al. |
| 4,623,627 A | 11/1986 | Huang et al. |
| 4,690,905 A | 9/1987 | Diamond et al. |
| 4,812,397 A | 3/1989 | Weisbart |
| 5,264,558 A | 11/1993 | Kim et al. |
| 5,959,084 A | 9/1999 | Ring |
| 6,485,977 B1 | 11/2002 | Colimer et al. |
| 7,189,396 B1 | 3/2007 | Weisbart |
| 7,378,092 B2 * | 5/2008 | Cohen ............... A61P 37/04 424/138.1 |
| 7,700,544 B2 | 4/2010 | Kisilevsky et al. |
| 9,701,740 B2 | 7/2017 | Hansen et al. |
| 2005/0079184 A1 | 4/2005 | Chang |
| 2008/0292618 A1 | 11/2008 | Weisbart et al. |
| 2010/0143358 A1 * | 6/2010 | Weisbart ............. A61P 35/00 424/134.1 |
| 2012/0070875 A1 | 3/2012 | Weisbart et al. |

FOREIGN PATENT DOCUMENTS

| | | |
|---|---|---|
| WO | WO 1997/32602 | 9/1997 |
| WO | WO 2010/138769 | 12/2010 |
| WO | WO 2012/135831 | 10/2012 |

OTHER PUBLICATIONS

Weisbart et al (Construction and expression of a bispecific single-chain antibody that penetrates mutant p53 colon cancer cells and binds p53, International Journal of Oncology, vol. 25, Published Oct. 2004). (Year: 2004).*
Hansen JE, et al. Antibody-mediated Hsp70 protein therapy. Brain Res. 2006 1088:187-96.
Hansen, et al., "Antibody-Mediated Transduction of Therapeutic Proteins into Living Cells," The Scientific World Journal (2005), 5:782-788.

(Continued)

*Primary Examiner* — Laura B Goddard
*Assistant Examiner* — Sarah A Alsomairy
(74) *Attorney, Agent, or Firm* — Ballard Spahr LLP

(57) ABSTRACT

The invention provides a method for inhibiting an intracellular target in a cell with a bispecific antibody comprising contacting the cell with a bispecific antibody having a first Fv fragment with a cell-penetrating determinant and a second Fv fragment with an intracellular target-binding determinant under suitable conditions so that the first Fv fragment causes the bispecific antibody to enter the cell and the second Fv fragment binds the intracellular target in the cell and thereby inhibiting the intracellular target.

5 Claims, 19 Drawing Sheets

Specification includes a Sequence Listing.

(56) References Cited

OTHER PUBLICATIONS

Kampinga, H.H., et al., Guidelines for the nomenclature of the human heat shock proteins, Cell Stress and chaperones (2009) 14:105-111.
Kang, EH et al., Downregulation of heat shock protein 70 protects rheumatoid arthritis fibroblast-like synoviocytes from nitric oxide-induced apoptosis. Arthritis Research Therapy 2009, 11:R130.
Kriangkum, J. et al., Bispecific and bifunctional single chain recombinant antibodies, Biomolecular Engineering, 18 (2001) 31-40.
PPICZα A, B, and C Pichia expression vectors for selection on Zeocin™ and purification of secreted, recombinant proteins. Invitrogen by Life Technologies, Jul. 7, 2010.
Weisbart, R.H., et al. Construction and expression of a bispecific single-chain antibody that penetrates mutant p53 colon cancer cells and binds p53. international Journal of Oncology, 25:1113-1118,, 2004.
Weisbart, R.H. et al., A Cell-Penetrating Bispecific Antibody for Therapeutic Regulation of Intracellular Targets, Molecular Cancer Therapeutics, American Association for Cancer Research, May 9, 2012, p. 1-5.
Zhan X, et al. Recombinant Fv-lisp70 protein mediates neuroprotection after focal cerebral ischemia in rats. Stroke 2010; 3:538-43.
U.S. Appl. No. 61/618,613, filed Mar. 30, 2012, Richard H. Weisbart.
U.S. Appl. No. 15/042,106 (U.S. Pat. No. 10,683,363), filed Feb. 11, 2016 (Jun. 16, 2020), Richard H. Weisbart (US Department of Veterans Affairs).
U.S. Appl. No. 13/844,318 (U.S. Pat. No. 9,283,272), filed Mar. 15, 2013 (Oct. 10, 2013), Richard H. Weisbart (US Department of Veterans Affairs).
U.S. Appl. No. 16/902,173, filed Jun. 15, 2020, Richard H. Weisbart (US Department of Veterans Affairs).
U.S. Appl. No. 18/322,846, filed May 24, 2023, Richard H. Weisbart (US Department of Veterans Affairs).

* cited by examiner

Fig. 1A
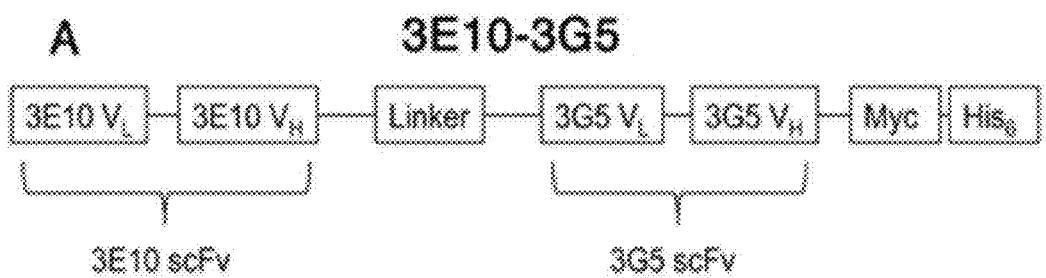
Fig. 1B
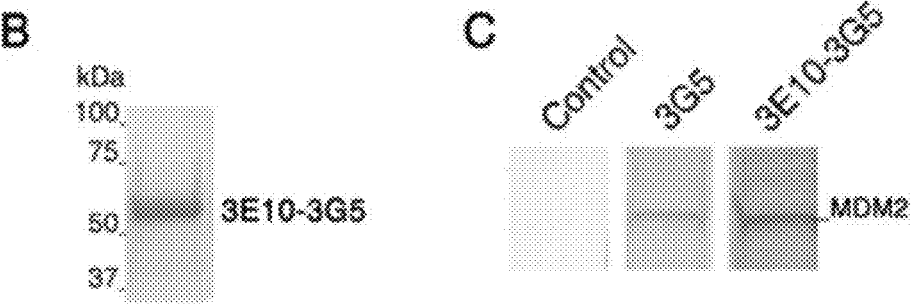
Fig. 1C
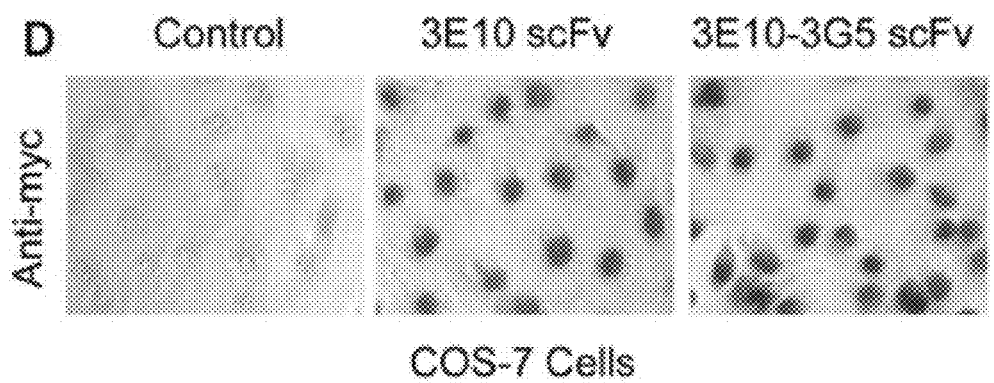
Fig. 1D

Fig. 2A
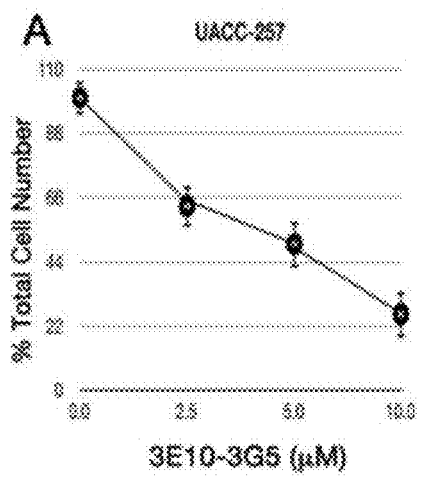
Fig. 2B
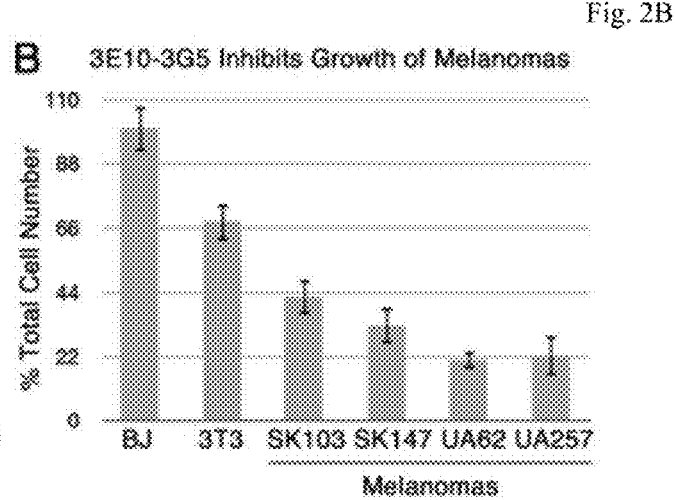
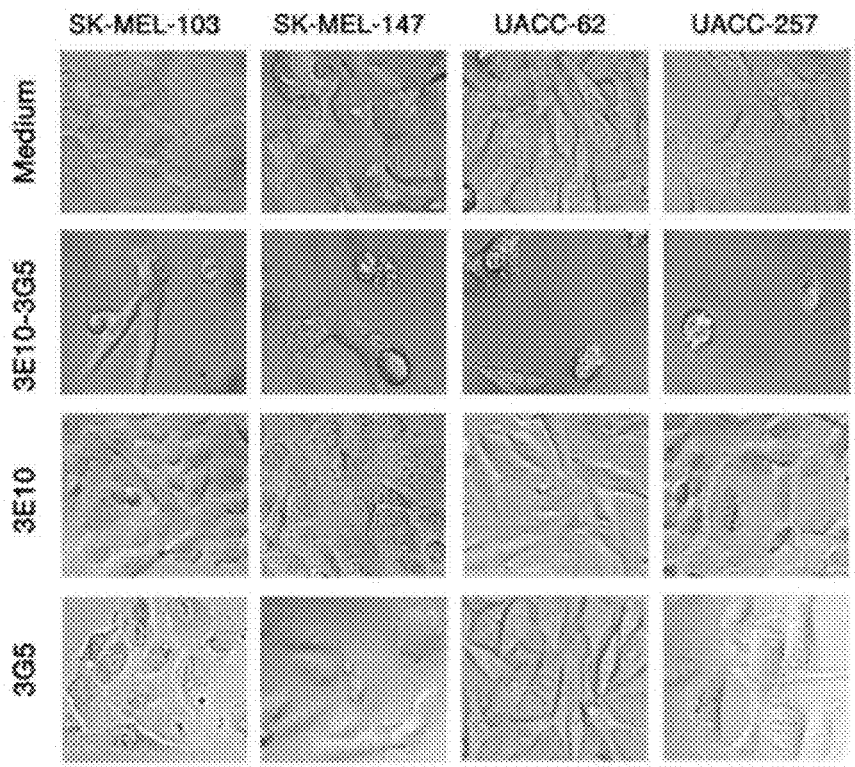
Fig. 2C

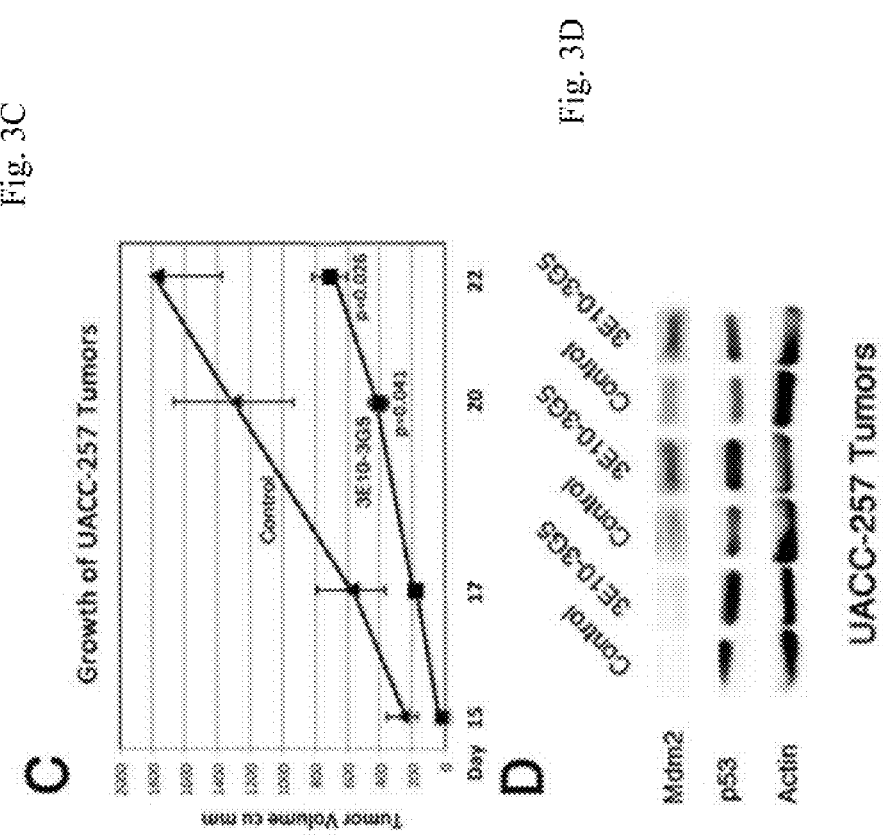
Fig. 3A
Fig. 3B
Fig. 3C
Fig. 3D
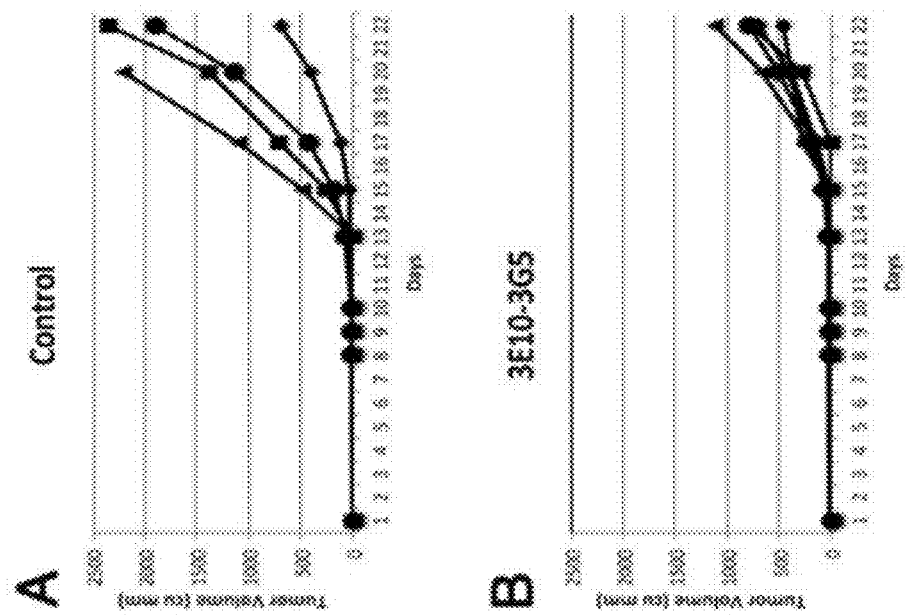

3E10-3G5 Bispecific scFv cloned between EcoRI and XbaI in pPicZαA pPicZαA α-factor signal sequence
ATG AGA TTT CCT TCA ATT TTT ACT GCT GTT TTA TTC GCA GCA TCC
 M   R   F   P   S   I   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A
                                    Kex2 signal cleavage →   End signal seq →

AAA GAA GGG GTA TCT CTC GAG AAA AGA GAG GCT GAA GCT
 K   E   G   V   S   L   E   K   R   E   A   E   A
                                                    ← Ste13 signal cleavage (AGIH Increases)  Begin 3E10
solubility       →
GCA GGA ATT CAC GAC ATT GTC CTG ACA CAG TCT CCT GCT TCC TTA
 A   G   I   H   D   I   V   L   T   Q   S   P   A   S   L
     *EcoRI*

Fig. 4

```
GCT GTA TCT CTG GGG CAG AGG GCC ACC ATC TCC TGC AGG GCC AGC
 A   V   S   L   G   Q   R   A   T   I   S   C   R   A   S
                                            |___3E10 Vk CDR1___
AAA AGT GTC AGT ACA TCT AGC TAT AGT ATG CAC TGG TAC CAA
 K   S   V   S   T   S   S   Y   S   M   H   W   Y   Q
_____|
CAG AAA CCA GGA CAG CCA CCC AAA CTC CTC ATC AAG TAT GCA TCC
 Q   K   P   G   Q   P   P   K   L   L   I   K   Y   A   S
                                            3E10 Vk CDR2
                                            |_____
TAC CTA GAA TCT GGG GTT CCT GCC AGG TTC AGT GGC AGT GGG TCT
 Y   L   E   S   G   V   P   A   R   F   S   G   S   G   S
____|
GGG ACA GAC TTC ACC CTC AAC ATC CAT CCT GTG GAG GAG GAT
 G   T   D   F   T   L   N   I   H   P   V   E   E   D
GCT GCA ACA TAT TAC TGT CAG CAC AGT AGG GAG TTT CCG TGG ACG
 A   A   T   Y   Y   C   Q   H   S   R   E   F   P   W   T
                        |___3E10 Vk CDR3_____
TTC GGT GGA GGC ACC AAG CTG GAA ATC AAA CGG GCT GAT GCT GCA
 F   G   G   G   T   K   L   E   I   K   R   A   D   A   A
____|
CCC GGG GGT GGC GGT TCT GGC GGT GGC GGA TCT GGA GGC GGT GGC
 P   G   G   G   G   S   G   G   G   G   S   G   G   G   G
         |_____(GGGGS)₃ Linker_____
```

Fig. 4, continued

```
TCT GAG GTG CAG CTG GTG GAG TCT GGG GGA GGC TTA GTG AAG CCT
S   E   V   Q   L   V   E   S   G   G   G   L   V   K   P

GGA GGG TCC CGG AAA CTC TCC TGT GCA GCC TCT GGA TTC ACT TTC
G   G   S   R   K   L   S   C   A   A   S   G   F   T   F

3E10 VH CDR1
AGT AAC TAT GGA ATG CAC TGG GTC CGT CAG GCT CCA GAG AAG GGG
S   N   Y   G   M   H   W   V   R   Q   A   P   E   K   G
(D31N mutation 3E10 VH enhances cell penetration)

3E10 VH CDR2
CTG GAG TGG GTT GCA TAC ATT AGT AGT GGC AGT AGT ACC ATC TAC
L   E   W   V   A   Y   I   S   S   G   S   S   T   I   Y

TAT GCA GAC ACA GTG AAG GGC CGA TTC ACC ATC TCC AGA GAC AAT
Y   A   D   T   V   K   G   R   F   T   I   S   R   D   N

GCC AAG AAC ACC CTG TTC CTG CAA ATG ACC AGT CTA AGG TCT GAG
A   K   N   T   L   F   L   Q   M   T   S   L   R   S   E

3E10 VH CDR3
GAC ACA GCC ATG TAT TAC TGT GCA AGG CGG GGG TTA CTA CTT GAC
D   T   A   M   Y   Y   C   A   R   R   G   L   L   L   D
```

Fig. 4, continued

TAC TGG GGC CAA GGC ACC ACT CTC ACA GTC TCC TCA GCT TCC ACC
 Y   W   G   Q   G   T   T   L   T   V   S   S   A   S   T
                                        End 3E10 →

Human CH1 Linker              Swivel Sequence
AAG GGC CCA TCC GTC TTC CCC CTG GCG CCC CTG GAG TCT TCC GGA
 K   G   P   S   V   F   P   L   A   P   L   E   S   S   G → Begin 3G5
TCC GAC ATC CAG ATG ACT CAG TCT CCA GCC TCC CTA TCT GTA TCT
 S   D   I   Q   M   T   Q   S   P   A   S   L   S   V   S 3G5 Vk CDR1
GTG GGA GAA ACT GTC ACC ATC ACA TGT CGA GCA AGT GAG AAT ATT
 V   G   E   T   V   T   I   T   C   R   A   S   E   N   I 3G5 Vk CDR2
TAC AGT AAT TTA GCA TGG TAT CAG CAG AAA CAG GGA AAA TCT CCT
 Y   S   N   L   A   W   Y   Q   Q   K   Q   G   K   S   P CAG CTC CTG GTG TAT GGT GCA ACA AAC TTA GCA GAT GGT GTC CCA
 Q   L   L   V   Y   G   A   T   N   L   A   D   G   V   P TCA AGG TTC AGT GGC AGT GGC TCA GGA ACA CAG TAT TCC CTC AAG
 S   R   F   S   G   S   G   S   G   T   Q   Y   S   L   K ATC AAC AGC CTG CAG TCT GAA GAT TTT GGG AGT TAT TAC TGT CAA
 I   N   S   L   Q   S   E   D   F   G   S   Y   Y   C   Q

Fig. 4, continued

3G5 Vk CDR3
```
CAT TTT TGG GGT ACT CCT CCG ACG TTC GGT GGA GGC ACC AAG CTG
 H   F   W   G   T   P   P   T   F   G   G   G   T   K   L
```

(GGGGS)₃ Linker
```
GAA CTC AAA AGG GCT GAT GCT GCA CCA GGA GGG GGA GGG TCT GGT
 E   L   K   R   A   D   A   A   P   G   G   G   G   S   G GGG GGC GGT TCC GGA GGC GGA GGC TCA GAG GTG CAA CTT GTT GAG
 G   G   G   S   G   G   G   G   S   E   V   Q   L   V   E TCT GGT GGA GGA TTG GTG CAG CCT AAA GGG TCA TTG AAA CTC TCA
 S   G   G   G   L   V   Q   P   K   G   S   L   K   L   S
```

3G5 VH CDR1
```
TGT GCA GCC TCT GGA TTC ACC TTC AAT ACC TAC GGC ATG AAC TGG
 C   A   A   S   G   F   T   F   N   T   Y   G   M   N   W

GTC CGC CAG GCT CCA GGA AAG GGT TTG GAA TGG GTC GGT CGC ATA
 V   R   Q   A   P   G   K   G   L   E   W   V   G   R   I
```

3G5 VH CDR2
```
AGA ACT AAA AAT AAT ATT TAT GCA ACA TAT TAT GAC GCT TCA GTG
 R   T   K   N   N   I   Y   A   T   Y   Y   D   A   S   V
```

Fig. 4, continued

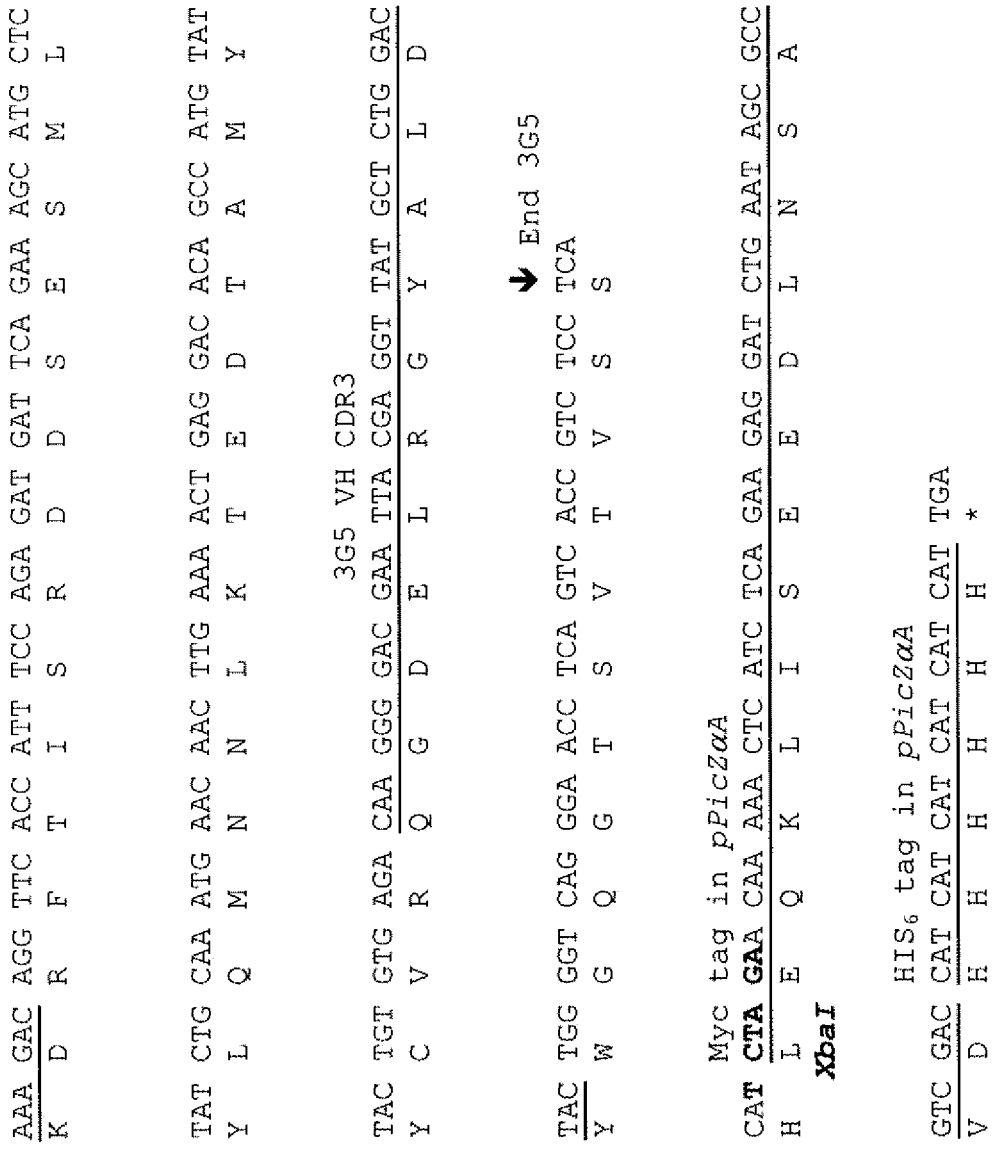
Fig. 4, continued

3E10-PAb421 (2012) Bispecific scFv cloned between EcoRI and XbaI in pPicZαA pPicZαA α-factor signal sequence
ATG AGA TTT CCT TCA ATT TTT ACT GCT GTT TTA TTC GCA GCA TCC
 M   R   F   P   S   I   F   T   A   V   L   F   A   A   S TCC GCA TTA GCT GCT CCA GTC AAC ACT ACA GAA GAT GAA ACG
 S   A   L   A   A   P   V   N   T   T   E   D   E   T GCA CAA ATT CCG GCT GAA GCT GTC ATC GGT TAC TCA GAT TTA GAA
 A   Q   I   P   A   E   A   V   I   G   Y   S   D   L   E GGG GAT TTC GAT GTT GCT GTT TTG CCA TTT TCC AAC AGC ACA AAT
 G   D   F   D   V   A   V   L   P   F   S   N   S   T   N AAC GGG TTA TTG TTT ATA AAT ACT ACT ATT GCC AGC ATT GCT GCT
 N   G   L   L   F   I   N   T   T   I   A   S   I   A   A Kex2 signal cleavage    End signal seq
AAA GAA GGG GTA TCT CTC GAG AAA AGA GAG GCT GAA GCT
 K   E   G   V   S   L   E   K   R   E   A   E   A
                                                            Ste13 signal cleavage sites (AGIH Increases)  Begin 3E10
solubility
GCA GGA ATT CAC GAC ATT GTC CTG ACA CAG TCT CCT GCT TCC TTA
 A   G   I   H   D   I   V   L   T   Q   S   P   A   S   L
    EcoRI

Fig. 5

```
GCT GTA TCT CTG GGG CAG AGG GCC ACC ATC TCC TGC AGG GCC AGC
 A   V   S   L   G   Q   R   A   T   I   S   C   R   A   S
                                 3E10 Vk CDR1
AAA AGT GTC AGT ACA TCT AGC TAT AGT TAC ATG CAC TGG TAC CAA
 K   S   V   S   T   S   S   Y   S   Y   M   H   W   Y   Q
                                                    3E10 Vk
CAG AAA CCA GGA CAG CCA CCC AAA CTC CTC ATC AAG TAT GCA TCC
 Q   K   P   G   Q   P   P   K   L   L   I   K   Y   A   S
CDR2
TAC CTA GAA TCT GGG GTT CCT GCC AGG TTC AGT GGC AGT GGG TCT
 Y   L   E   S   G   V   P   A   R   F   S   G   S   G   S
GGG ACA GAC TTC ACC CTC AAC ATC CAT CCT GTG GAG GAG GAG GAT
 G   T   D   F   T   L   N   I   H   P   V   E   E   E   D
                                 3E10 Vk CDR3
GCT GCA ACA TAT TAC TGT CAG CAC AGT AGG GAG TTT CCG TGG ACG
 A   A   T   Y   Y   C   Q   H   S   R   E   F   P   W   T
TTC GGT GGA GGC ACC AAG CTG GAA ATC AAA CGG GCT GAT GCT GCA
 F   G   G   G   T   K   L   E   I   K   R   A   D   A   A
            (GGGGS)3 Linker
CCC GGG GGT GGC GGT TCT GGC GGT GGC GGT TCT GGA GGC GGT GGC
 P   G   G   G   G   S   G   G   G   G   S   G   G   G   G
```

Fig. 5, continued

```
TCT GAG GTG CAG CTG GTG GAG TCT GGG GGA GGC TTA GTG AAG CCT
S   E   V   Q   L   V   E   S   G   G   G   L   V   K   P

GGA GGG TCC CGG AAA CTC TCC TGT GCA GCC TCT GGA TTC ACT TTC
G   G   S   R   K   L   S   C   A   A   S   G   F   T   F

3E10 VH CDR1
AGT AAC TAT GGA ATG CAC TGG GTC CGT CAG GCT CCA GAG AAG GGG
S   N   Y   G   M   H   W   V   R   Q   A   P   E   K   G
(D31N mutation 3E10 VH enhances cell penetration)

3E10 VH CDR2
CTG GAG TGG GTT GCA TAC ATT AGT AGT GGC AGT AGT ACC ATC TAC
L   E   W   V   A   Y   I   S   S   G   S   S   T   I   Y

TAT GCA GAC ACA GTG AAG GGC CGA TTC ACC ATC TCC AGA GAC AAT
Y   A   D   T   V   K   G   R   F   T   I   S   R   D   N

GCC AAG AAC ACC CTG TTC CTG CAA ATG ACC AGT CTA AGG TCT GAG
A   K   N   T   L   F   L   Q   M   T   S   L   R   S   E

3E10 VH CDR3
GAC ACA GCC ATG TAT TAC TGT GCA AGG CGG GGG TTA CTA CTT GAC
D   T   A   M   Y   Y   C   A   R   R   G   L   L   L   D
```

Fig. 5, continued

```
                                          End 3E10 →
TAC TGG GGC CAA GGC ACC ACT CTC ACA GTC TCC TCA GCT TCC ACC
 Y   W   G   Q   G   T   T   L   T   V   S   S   A   S   T

Human CH1 Linker                         Swivel Sequence
AAG GGC CCA TCC GTC TTC CCC CTG GCG CCC CTG GAG TCT TCC GGA
 K   G   P   S   V   F   P   L   A   P   L   E   S   S   G → Begin PAb421
TCC GAT GTT GTG ATG ACC CAG ACT CCA CTC ACT TTG TCG GTT ACC
 S   D   V   V   M   T   Q   T   P   L   T   L   S   V   T PAb421 Vk CDR1
CCT GGA CAA CCA GCC TCC ATC TCT TGC AAG TCA AGT CAG AGC CTC
 P   G   Q   P   A   S   I   S   C   K   S   S   Q   S   L TTG GAT AGT GAT GGA AAG ACA TAC TTG AAT TGG TTG TTA CAG AGG
 L   D   S   D   G   K   T   Y   L   N   W   L   L   Q   R PAb421 Vk CDR2
CCA GGC CAG TCT CCA AAG CGC CTA ATC TAT CTG GTG TCT AAA CTG
 P   G   Q   S   P   K   R   L   I   Y   L   V   S   K   L GAC TCT GGA GTC CCT GAC AGG TTC ACT GGC AGT GGA TCA GGG ACA
 D   S   G   V   P   D   R   F   T   G   S   G   S   G   T GAT TTC ACA CTG AAA ATC AAC AGA GTG GAG GCT GAG GAT TTG GGA
 D   F   T   L   K   I   N   R   V   E   A   E   D   L   G
```

Fig. 5, continued

PAb421 Vk CDR3
GTT TAT TAT TGC TGG CAA GGT ACA CAT TCT CCG CTC ACG TTC GGT
 V   Y   Y   C   W   Q   G   T   H   S   P   L   T   F   G

GCT GGC ACC AAG CTG GAA ATT AAA CGG GCT GAC GCT GCA CCC GGG
 A   G   T   K   L   E   I   K   R   A   D   A   A   P   G (GGGGS)₃ Linker
GGA GGG GGA TCT GGT GGC GGC GGA TCA GGT GGA GGT GGA TCT CAG
 G   G   G   S   G   G   G   S   G   G   G   G   S   Q GTG CAG CTG CAG CAG TCT GGG GCA GAG CTT GTG AGG TCA GGG GCC
 V   Q   L   Q   Q   S   G   A   E   L   V   R   S   G   A TCA GTC AAG TTG TCC TGC ACA GCT TCT GGC TTC AAC ATT AAA GAC
 S   V   K   L   S   C   T   A   S   G   F   N   I   K   D PAb421 VH CDR1
TAC TAT ATG CAC TGG GTG AAG CAG AGG CCT GAA CAG GGC CTG GAG
 Y   Y   M   H   W   V   K   Q   R   P   E   Q   G   L   E PAb421 VH CDR2
TGG ATT GGA TGG ATT GAT CCT GAG AAT GGT GAT ACT GAA TAT GCC
 W   I   G   W   I   D   P   E   N   G   D   T   E   Y   A CCG AAG TTC CAG GGC AAG GCC ACT ATG ACT GCA GAC ACA TCC TCC
 P   K   F   Q   G   K   A   T   M   T   A   D   T   S   S

Fig. 5, continued

Fig. 5, continued

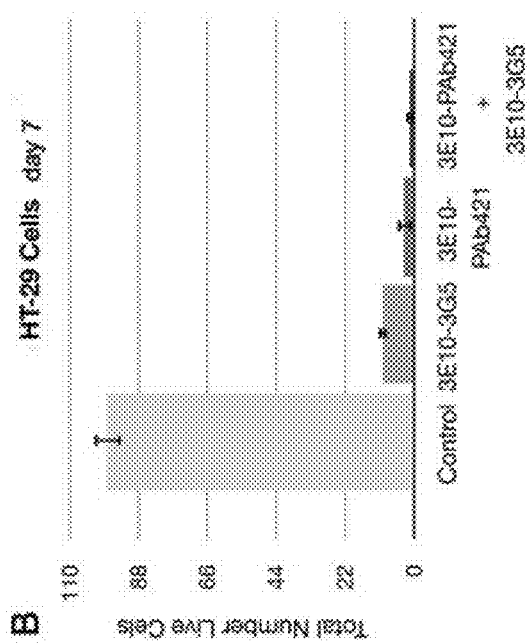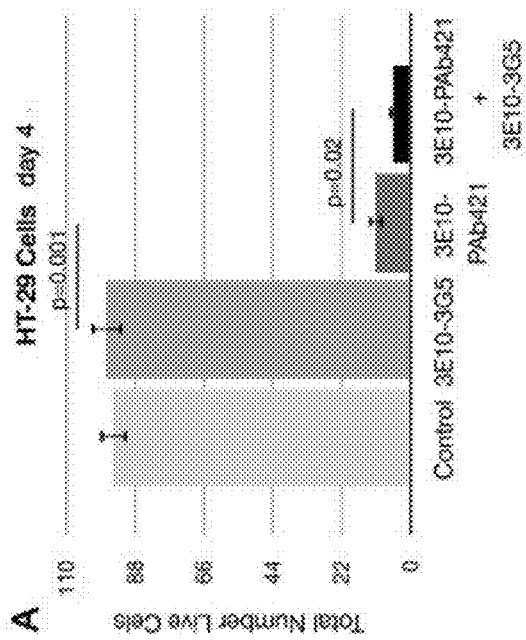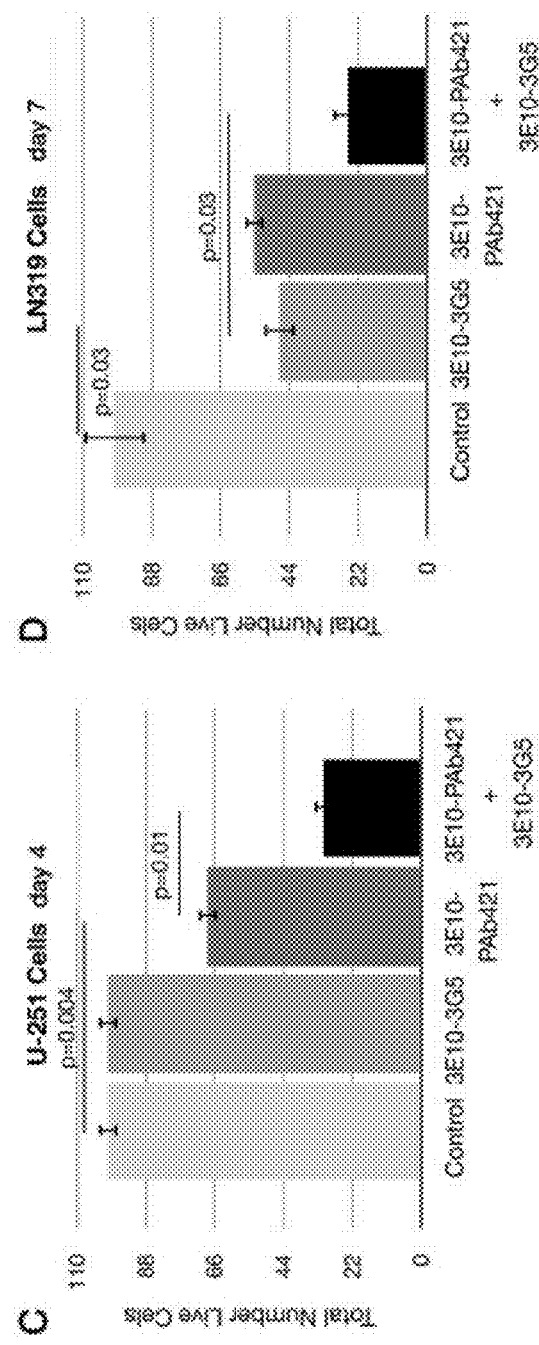

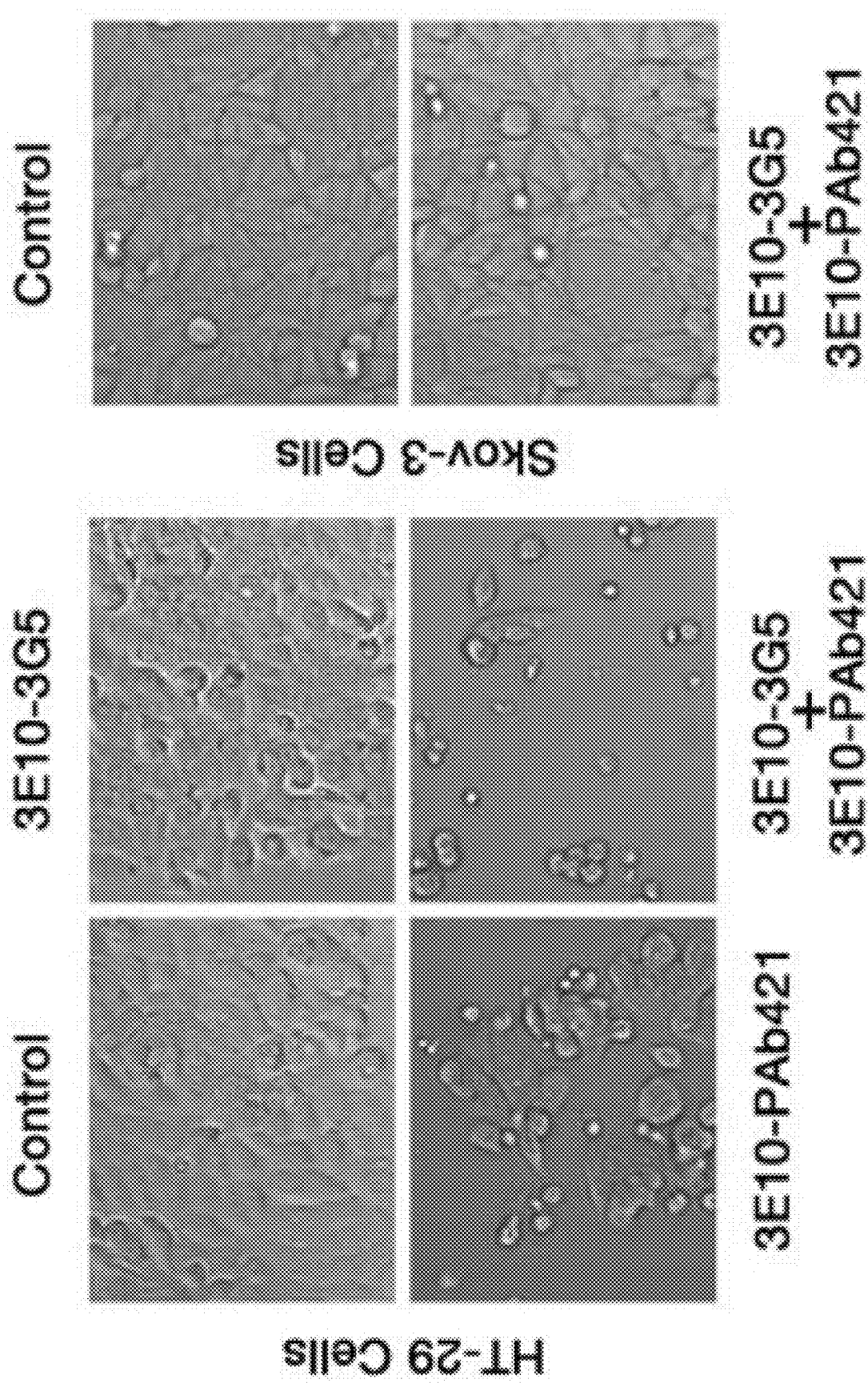

TARGETING INTRACELLULAR TARGET-BINDING DETERMINANTS WITH INTRACELLULAR ANTIBODIES

CROSS-REFERENCE TO RELATED APPLICATIONS

This patent application is a continuation of U.S. application Ser. No. 18/322,846, filed May 24, 2023, which is a continuation of U.S. application Ser. No. 16/902.173, filed Jun. 15, 2020, which is a continuation of U.S. application Ser. No. 15/042.106, filed Feb. 11, 2016 (now U.S. Pat. No. 10,686,363), which is a divisional of U.S. of application Ser. No. 13/844,318, filed Mar. 15, 2013 (now U.S. Pat. 9,283,272), and which claims the benefit of the filing date of U.S. Provisional Application No. 61/618,613, filed Mar. 30, 2012. The content of these earlier filed applications is hereby incorporated herein by reference in its entirety.

SEQUENCE LISTING

The present application contains a Sequence Listing that is submitted concurrent with the filing of this application in XML file format, containing the file name "37759_0150U6_Sequence_Listing.xml" which is 118,784 bytes in size, created on Sep. 27, 2023. The Sequence Listing is hereby incorporated by reference into the present application in its entirety.

Throughout this application various publications are referenced. The disclosures of these publications in their entireties are hereby incorporated by reference into this application in order to more fully describe the state of the art to which this invention pertains.

BACKGROUND OF THE INVENTION

Current therapies are largely based on the use of small molecules to target intracellular sites, because cells are impervious to large molecules such as proteins. However, small molecule inhibitors are prone to have undesirable side effects as a result of binding unintended targets. By contrast, antibodies have excellent binding specificity, but most do not penetrate living cells. Thus, the current use of therapeutic antibodies is limited to targeting molecules that are secreted or located on the cell membrane. Intracellular antibodies can be generated by gene therapy, but the potential dangers have not justified its use. Cell-penetrating peptides (CPPs) also referred to as protein transduction domains (PTDs) are currently used to transport proteins into cells (Chugh A, Eudes F, Shim Y-S. Cell-penetrating peptides: Nanocarrier for macromolecule delivery in living cells. IUBMB Life, 62: 183-193, 2010). However, an important limitation of these intracellular transporters is that they may be targeted to endosomes through lipid rafts. In addition, some are highly cationic peptides that have been shown to be toxic to normal cells (Toborek, M; Lee, Y W; Pu, H; Malecki, A; Flora, G; Garrido, R; Hennig, B; Bauer, H C; Nath, A. HIV-Tat protein induces oxidative and inflammatory pathways in brain endothelium. *J. Neurochem.* 2003; 84(1), 169-179; Pu, H; Tian, J; Flora, G; Lec, Y W; Nath, A; Hennig, B; Toborek, M. HIV-1 Tat protein upregulates inflammatory mediators and induces monocyte invasion into the brain. *Mol. Cell. Neurosci.* 2003). We identified a unique monoclonal anti-DNA antibody, mAb 3E10 described (Weisbart R H, et al. *J Immunol.* 1990 144(7): 2653-2658; ATCC Accession No. PTA 2439 hybridoma), which penetrates living cells and localizes in the nucleus without apparent harm (Zack, D. J., Stempniak, M., Wong. A. L., Taylor, C., Weisbart, R. H.: Mechanisms of cellular penetration and nuclear localization of an anti-double strand DNA autoantibody. J. Immunol., 157:2082-2088, 1996). In contrast to CCPs, mAb 3E10 and its single-chain Fv fragment (scFv) are internalized through hENT2, an equilibrative nucleoside salvage pathway (Hansen J E, Tse C M, Chan G, Heinze E R, Nishimura R N, Weisbart R H. Intranuclear protein transduction through a nucleoside salvage pathway. J Biol Chem. 2007 Jul. 20; 282(29):20790-3. Epub 2007 May 24). hENT2 is expressed in most cells, but its expression is increased in muscle and cancer cells. On the basis of these findings, we developed the Fv fragment of 3E10 as an intracellular delivery system for large molecules (Weisbart, R. H., Stempniak, M., Harris, S., Zack, D. J., and Ferreri, K.: An autoantibody is modified for use as a delivery system to target the cell nucleus: Therapeutic implications. J. Autoimmun., 11:539-546, 1998; Weisbart, R. H., Baldwin, R., Huh, B., Zack, D. J., and Nishimura, R.: Novel protein transfection of primary rat cortical neurons utilizing an antibody that penetrates living cells. J. Immunol., 164:6020-6026, 2000; Weisbart, R. H., Wakelin, R., Chan, G., Miller, C. W. and Koeffler, P. H. Construction and expression of a bispecific single-chain antibody that penetrates mutant p53 colon cancer cells and binds p53. International Journal of Oncology, Int. J. Onc. 25:1113-1118, 2004; Weisbart, R. H., Hansen, J., Chan, G., Wakellin, R., Chang. S., Heinze, E., Miller, C. W., Koeffler, H. P., Yang, F., Cole, G. M., Min, Y., and Nishimura, R. Antibody-mediated transduction of p53 into cancer cells. Int. J. Onc. 25:1867-1873, 2004; Hansen J E, Sohn W., Kim C, Chang S S, Huang N C, Santos D G, Chan G, Weisbart R H, Nishimura R N. Antibody-mediated Hsp70 protein therapy. Brain Res. 2006 1088:187-96; Hansen, J E; Fischer, L K; Chan, G; Chang, S S; Baldwin, S W; Aragon, R J; Carter, J J; Lilly, M; Nishimura, R N; Reeves, M E; Weisbart, R H. Antibody-mediated p53 protein therapy prevents liver metastasis in vivo. Cancer Res. 2007; 67(4); Heinze E, Baldwin S, Chan G, Hansen J, Song J. Clements D, Aragon R, Nishimura R, Reeves M, Weisbart R. Antibody-mediated FOXP3 protein therapy induces apoptosis in cancer cells in vitro and inhibits metastasis in vivo. Int J Oncol. 2009 July; 35(1):167-73; Heinze E, Chan G, Mory R, Khavari R, Alavi A, Chung S Y, Nishimura R N, Weisbart R H. Tumor suppressor and T-regulatory functions of Foxp3 are mediated through separate signaling pathways. Oncology Letters. Published online May, 2011). After localizing in the cell nucleus, 3E10 scFv is largely degraded within 4 hours, thus minimizing potential toxicity.

The exquisite specificity of antibody-antigen interactions is ideal for therapeutic applications, but the therapeutic use of antibodies is limited to extracellular targets because of limited access of antibodies into cells. We developed a method to deliver antibodies into cells as bispecific single-chain Fv fragments constructed with the Fv fragment of a cell-penetrating monoclonal antibody, 3E10, which localizes to the nucleus. Since Mdm2 is an important cancer target, we selected an anti-Mdm2 monoclonal antibody, mAb 3G5, for intracellular transport to target Mdm2-dependent cancer cells. 3G5 was shown previously to bind critical residues L66, Y67, and E69 at the N-terminus of Mdm2 required for binding to p53, and was, therefore, an excellent candidate to serve as a competitive inhibitor of Mdm2 (Chen J, Marechal V, and Levine, A J. Mapping of the p53 and mdm-2 Interaction Domains. Molecular and Cellular Biology, 13:4107-4114, 1993; Bottger A, Bottger V, Garcia-Echeverria C, Chene P, Hochkeppel H K, Sampson W, Ang K., Howard, S F., Picksley S M, Lane D P. Molecular characterization of the hdm2-p53 interaction. J. Mol. Biol. 269: 744-56, 2007; Elizabeth Rayburn, Ruiwen Zhang, Jie He and Hui Wang. MDM2 and Human Malignancies: Expression, Clinical Pathology, Prognostic Markers, and Implications for Chemotherapy. Current Cancer Drug Targets, 5:27-41, 2005; Shangary S and Wang S. Small-molecule inhibitors of the MDM2-p53 protein-protein interaction to reactivate p53 function: a novel approach for cancer therapy. Annu. Rev. Pharmacol. Toxicol. 49:223-41, 2009; Lane, D P. New insights into p53 based therapy. Discovery Medicine. Published online, Aug. 18, 2011). Mdm2 is an E3 ubiquitin ligase that down-regulates p53 function, but it also has p53-independent growth-inhibitory functions.

Our invention demonstrates the feasibility of transporting antibodies into cells for therapeutic regulation of intracellular targets and the possibility for enhanced or synergistic inhibition of the growth of tumor cells when multiple components of a regulatory pathway are targeted with more than one therapeutic agent; furthermore, our invention provides novel reagents for treatment of tumors, cancers, diseases and disregulated processes along with a rationale for their combined use in targeting a regulatory pathway disregulated in tumor cells, or alternatively, components of any number of pathways that might be disregulated within tumors, cancers, diseases or conditions.

SUMMARY OF THE INVENTION

The invention provides bispecific antibodies having Fv fragments with a cell-penetrating determinant and a second Fv fragment with an intracellular target-binding determinant. In one embodiment, the intracellular target-binding determinant is an E3 ubiquitin-protein ligase, or tumor suppressor-interacting protein, such as MDM2. In one embodiment, the intracellular target-binding determinant may target an oncoprotein such as a myc or ras oncoprotein. In another embodiment, the intracellular target-binding determinant may target DNA repair proteins such as a RAD52 protein, ataxia telangiectasia mutated protein (ATM), CHK2 or CHK1 proteins, BCL2 protein. Additional examples of proteins associated with DNA repair include but are not limited BRCA1, MDC1, 53BP1, p53, ATR, and p21.

In one embodiment, the Fv fragment with the cell penetrating determinant is a 3E10 Fv. Additionally, in one embodiment the second Fv fragment with an intracellular target-binding determinant is a 3G5 Fv.

The 3E10 bispecific antibodies of the invention may further comprise one or more amino acid sequence comprising Ala-Gly-Ile-His (AGIH) at the amino terminus of one or both of the Fv region.

The 3E10 bispecific antibodies of the invention may be joined or attached to localizing signals so as to direct the scFvs to intracellular compartments such as endoplasmic reticulum and mitochondria. Further, the 3E10 bispecific antibodies of the invention may incorporate enzyme cleavage sites to separate the scFvs once they are transported into cells. Additionally, the 3E10 bispecific antibodies of the invention may be joined to produce bispecific scFvs that bind peptides attached to siRNAs as a method to use bispecific scFvs to transport siRNA into cells.

The invention provides method for regulating intracellular targets with a bispecific antibody comprising contacting a cell with a bispecific antibody having a Fv fragment with a cell-penetrating determinant and a second Fv fragment with an intracellular target-binding determinant.

The invention provides a method for inhibiting an intracellular target in a cell with a bispecific antibody comprising contacting the cell with a bispecific antibody having a first recombinant variable region of an immunoglobulin molecule with a cell-penetrating determinant (e.g. Fv fragment of mAb 3E10). Preferably the first recombinant variable region causes the bispecific antibody to enter the cell. Additionally, the bispecific antibody has a second recombinant variable region of an immunoglobulin molecule with an intracellular target-binding determinant (e.g. Fv fragment of mAb 3G5) under suitable conditions so that it binds the intracellular target in the cell so that the bispecific antibody inhibits the intracellular target.

The invention provides a method for inhibiting an intracellular target in a cell with a bispecific antibody comprising contacting the cell with a bispecific antibody having a first Fv fragment with a cell-penetrating determinant and a second Fv fragment with an intracellular target-binding determinant under suitable conditions so that the first Fv fragment causes the bispecific antibody to enter the cell and the second Fv fragment binds the intracellular target in the cell and thereby inhibiting the intracellular target.

The invention also provides a method for increasing p53 tumor suppressor protein levels in a tumor or cancer cell by exposing the cancer cell with a bispecific antibody having a first Fv fragment with a cell-penetrating determinant and a second Fv fragment with an intracellular target-binding determinant, thereby increasing the level of p53 tumor suppressor protein levels in a tumor or cancer cell.

The invention further provides a method for inhibiting the growth of MDM2-addicted tumor or cancer cells in a subject by exposing the tumor or cancer cell to a bispecific antibody comprising a Fv fragment with a cell-penetrating determinant of anti-DNA monoclonal antibody 3E10 and a second Fv fragment with an intracellular target-binding determinant for MDM2, thereby inhibiting the growth of tumor or cancer cells in the subject.

The invention also provides a method for regulating activity of MDM2-interacting proteins with a bispecific antibody comprising contacting a cell with a bispecific antibody having a Fv fragment with a cell-penetrating determinant and a second Fv fragment with a binding determinant for MDM2.

The invention further provides a method for increasing therapeutic effectiveness of treating tumor, cancer or a dis-regulated intracellular process comprising the use of combination therapy with a bispecific antibody comprising: (a) a Fv fragment with a cell-penetrating determinant and a second Fv fragment with an intracellular target-binding determinant, and (b) a second bispecific antibody comprising a Fv fragment with a cell-penetrating determinant and an additional second Fv fragment with an intracellular target-binding determinant for a second protein of the same biochemical pathway, intracellular signaling pathway, or regulatory network.

In one embodiment, the invention provides a bispecific antibody comprising a first Fv fragment with a cell-penetrating determinant from an anti-DNA monoclonal antibody 3E10 or an antibody which competes with monoclonal antibody 3E10 and a second Fv fragment with an intracellular target-binding determinant that inhibits the biological activity, biochemical activity, regulatory activity or cellular signal associated with the determinant or a macromolecule to which the determinant is attached.

In one embodiment, the invention provides a bispecific antibody having the amino acid sequence of SEQ ID NO:2.

In another embodiment, the invention provides a bispecific antibody encoded by nucleic acid sequence, as shown in SEQ ID NO:1.

In yet another embodiment, the invention provides a bispecific antibody comprising one or more of amino acid sequence of SEQ ID NOS:3, 5, 7, 9, 11, 13, 15, 17, 19, 21, 23, 25, or 27.

In a further embodiment, the invention provides a bispecific antibody encoded by a nucleic acid sequence, comprising nucleic acid sequence as shown in SEQ ID NO:1 from nucleotide position 268 to 1833, or SEQ ID NOS:4, 6, 8, 10, 12, 14, 16, 18, 20, 22, 24, or 26.

In one embodiment, the invention provides a second bispecific antibody having the amino acid sequence of SEQ ID NO:29.

In another embodiment, the invention provides a second bispecific antibody encoded by nucleic acid sequence, as shown in SEQ ID NO:28.

In yet another embodiment, the invention provides a bispecific antibody comprising one or more of amino acid sequence of SEQ ID NOS:30, 5, 7, 9, 11, 13, 15, 32, 34, 36, 38, 40, or 42.

In a further embodiment, the invention provides a bispecific antibody encoded by a nucleic acid sequence, comprising nucleic acid sequence as shown in SEQ ID NO:28 from nucleotide position 268 to 1827, or SEQ ID NOS:4, 6, 8, 10, 12, 14, 31, 33, 35, 37, 39, or 41.

In additional embodiment, the invention contemplates disclosed amino acid sequence of a bispecific antibody comprising conservative amino acid substitution or substitutions.

In additional embodiment, the invention contemplates disclosed nucleic acid sequence for a bispecific antibody comprising silent mutation or mutations.

The invention also provides a bispecific antibody or a single chain antibody comprising one or more of gly-gly-gly-gly-serine repeat(s), human CH1 linker, and a swivel sequence.

BRIEF DESCRIPTION OF THE FIGURES

FIGS. 1A-D show that the 3E10-3G5 bispecific antibody retains the MDM2-binding activity of 3G5 and the cell-penetrating activity of 3E10. FIG. 1A is a schematic of the 3E10-3G5 bispecific antibody. FIG. 1B shows purified 3E10-3G5 visualized by SDS-PAGE and GelCode Blue® staining. A single band is observed at the expected molecular weight of ~60 kDa. FIG. 1C shows Western blots of MC-7 cell lysates probed with control, 3G5, or 3E10-3G5 demonstrate that both 3G5 and 3E10-3G5 recognize and bind MDM2. FIG. 1D shows that 3E10-3G5 penetrates COS-7 cells and localizes to the nucleus similar to 3E10 scFv alone as evidenced by anti-myc staining.

FIGS. 2A-C show that 3E10-3G5 impairs the growth of MDM2-addicted melanoma cells. FIG. 2A shows the dose-response effect of 3E10-3G5 on growth of UACC-257 cells. Shown is mean response±S.D. of duplicate determinations. There was no effect of 3E10 or 3G5 alone. FIG. 2B shows that the growth of human melanoma cells (SK-MEL-103, SK-MEL-147, UACC-62, UACC-257) was inhibited at day 3 by 10 µM 3E10-3G5 compared to medium alone. Results are representative of 3 independent experiments and are shown as mean±S.D. 3T3 are transformed mouse fibroblasts, and BJ is a culture of normal human primary fibroblasts. FIG. 2C shows microscopy images demonstrating the differences in cell population and morphology of melanoma cells 3 days after treatment with 3E10-3G5 compared to control buffer, 3E10 alone, and 3G5 alone.

FIGS. 3A-D show that 3E10-3G5 inhibits human melanoma xenograft growth in vivo. Nude mice were injected subcutaneously with $1\times10^6$ UACC-257 cells on day 1 and then observed (FIG. 3A) control group or (FIG. 3B) treated by i.p. administration of 1.0 mg 3E10-3G5 on days 1-4. FIG. 3C shows the mean tumor volume±SEM after injection of cells into control and treated mice. FIG. 3D shows that tumors in mice treated with 3E10-3G5 exhibit increased levels of p53 and MDM2 as demonstrated by Western blotting for p53 and MDM2 in tumors from three control and three 3E10-3G5-treated mice.

FIG. 4 shows the sequence of 3E10-3G5 bispecific scFv cloned between EcoRI and XbaI in pPicZαA. FIG. 4 shows the nucleic acid sequence provided in SEQ ID NO: 1 and the encoded polypeptide sequence in SEQ ID NO: 2.

FIG. 5 shows the sequence of 3E10-PAb421 bispecific scFv cloned between EcoRI and XbaI in pPicZαA. FIG. 5 shows the nucleic acid sequence provided in SEQ ID NO: 28 and the encoded polypeptide sequence in SEQ ID NO: 29.

FIGS. 7A-D show bar graphs of (FIG. 7A) HT-29 cells on day 4; (FIG. 7B) HT-29 cells on day 7; (FIG. 7C) U-251 cells on day 4; and (FIG. 7D) LN319 cells on day 7 in which combined 3E10-3G5 and 3E10-PAb421 bispecific antibody treatment results in enhanced or synergistic inhibition on growth of human cancer cells in vitro.

FIGS. 8A-B show photomicrographs of a synergistic cytotoxic effect of 3E10-3G5 and 3E10-PAb421 bispecific antibody treatment on HT-29 cells in vitro. Unlike HT-29 (FIG. 8A), a human ovarian cell line, Skov-3 (FIG. 8B), does not appear to be affected morphologically by the combined treatment; Skov-3 does not express p53 protein.

Figure 6A:
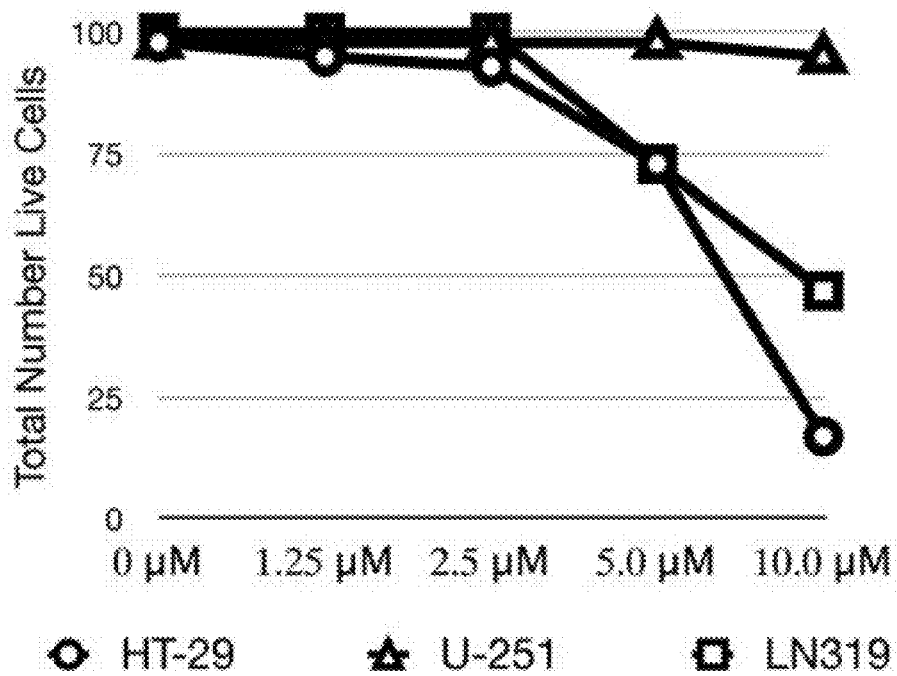
FIGS. 6A-B show line graphs of (FIG. 6A) 3E10-3G5 scFv dose response and (FIG. 6B) 3E10-Pab421 scFv dose response on growth of a human colon cancer cell line (HT29), a human glioblastoma cell line (U251) and a human astrocytoma cell line (LN-319) in vitro.

Summary Table of SEQ ID NO and Description

| SEQ ID NO: | DESCRIPTION |
|---|---|
| 1 | 3E10-3G5 coding sequence with initiator and epitope tags nucleic and amino acid |
| 2 | 3E10-3G5 coding sequence with initiator and epitope tags amino acid |
| 3 | 3E10-3G5 bispecific antibody with AGIH and no initiator or epitope tags amino acid |
| 4 | 3E10 kappa light chain CDR1 nucleic and amino acid |
| 5 | 3E10 kappa light chain CDR1 amino acid |
| 6 | 3E10 kappa light chain CDR2 nucleic and amino acid |
| 7 | 3E10 kappa light chain CDR2 amino acid |
| 8 | 3E10 kappa light chain CDR3 nucleic and amino acid |
| 9 | 3E10 kappa light chain CDR3 amino acid |
| 10 | 3E10 VH chain CDR1 with D31N mutation nucleic and amino acid |
| 11 | 3E10 VH chain CDR1 with D31N mutation amino acid |
| 12 | 3E10 VH chain CDR2 nucleic and amino acid |
| 13 | 3E10 VH chain CDR2 amino acid |
| 14 | 3E10 VH chain CDR3 nucleic and amino acid |
| 15 | 3E10 VH chain CDR3 amino acid |
| 16 | 3G5 kappa light chain CDR1 nucleic and amino acid |
| 17 | 3G5 kappa light chain CDR1 amino acid |
| 18 | 3G5 kappa light chain CDR2 nucleic and amino acid |
| 19 | 3G5 kappa light chain CDR2 amino acid |
| 20 | 3G5 kappa light chain CDR3 nucleic and amino acid |
| 21 | 3G5 kappa light chain CDR3 amino acid |
| 22 | 3G5 VH chain CDR1 nucleic and amino acid |
| 23 | 3G5 VH chain CDR1 amino acid |
| 24 | 3G5 VH chain CDR2 nucleic and amino acid |

-continued

Summary Table of SEQ ID NO and Description

| SEQ ID NO: | DESCRIPTION |
|---|---|
| 25 | 3G5 VH chain CDR2 amino acid |
| 26 | 3G5 VH chain CDR3 nucleic and amino acid |
| 27 | 3G5 VH chain CDR3 amino acid |
| 28 | 3E10-PAb421 complete coding sequence with initiator and epitope tags nucleic and amino acid |
| 29 | 3E10-PAb421 complete coding sequence with initiator and epitope tags amino acid |
| 30 | 3E10-PAb421 bispecific antibody with AGIH and no initiator or epitope tag amino acid |
| 31 | PAb421 kappa light chain CDR1 nucleic and amino acid |
| 32 | PAb421 kappa light chain CDR1 amino acid |
| 33 | PAb421 kappa light chain CDR2 nucleic and amino acid |
| 34 | PAb421 kappa light chain CDR2 amino acid |
| 35 | PAb421 kappa light chain CDR3 nucleic and amino acid |
| 36 | PAb421 kappa light chain CDR3 amino acid |
| 37 | PAb421 VH chain CDR1 nucleic and amino acid |
| 38 | PAb421 VH chain CDR1 amino acid |
| 39 | PAb421 VH chain CDR2 nucleic and amino acid |
| 40 | PAb421 VH chain CDR2 amino acid |
| 41 | PAb421 VH chain CDR3 nucleic and amino acid |
| 42 | PAb421 VH chain CDR3 amino acid |

DETAILED DESCRIPTION OF THE INVENTION

Definitions

To facilitate understanding of the invention, a number of terms are defined below.

As used herein, a "bispecific antibody" means any immunologically reactive molecule which specifically recognizes and binds at least two different targets at alternate times or at the same time. The immunologically reactive molecule may be a single polypeptide chain as for example in bispecific antibody comprising two or more single chain Fv (scFv) fragments. The immunologically reactive molecule may consist of more than one polypeptide chains such as bispecific antibodies created from two antibodies with differing antigen specificity held together by disulfide bonds, chemical crosslinkers, or bridging agents which function to bring the two different antibodies together.

Typically, a "bispecific antibody" will contain the variable region of a heavy chain and a light chain or portions thereof to permit recognition of a target as well as a second variable region of a heavy chain and a light chain or portions thereof of an antibody to permit recognition of a second target.

The "bispecific antibody" may also include a constant region of heavy and/or light chain. However, a constant region is optional. Also, when the bispecific antibody includes a constant region of a heavy and/or light chain, it may be the entire constant region or a portion thereof.

A "bispecific antibody" also includes its equivalent, in which at least one determinant of the "bispecific antibody" is replaced with a non immunoglobulin sequence-related polypeptide or agent that recognizes one or more of the targets. Such non immunoglobulin sequence-related peptide or agent could be discovered through screening of phage display libraries, peptide libraries, cDNA libraries or non-peptide libraries, such as cell penetrating peptides or aptamers. In addition to peptides or aptamers, non immunoglobulin sequence-related agent could include nucleic acid, RNA or DNA, as well as carbohydrate or lipid and their derivatives.

A "bispecific antibody" includes heteroconjugates with binding specificities for at least two different targets. For example a heteroconjugates includes a hybrid antibody created from linking two different antibodies or antibody fragments or a hybrid of an antibody or antibody fragment linked to a lectin or lectin fragment or another determinant with an intracellular binding specificity or a cell penetrating ability, so long as the heteroconjugates have binding specificities for at least two targets.

A "bispecific antibody" includes heteroconjugates in which a "bispecific antibody" is coupled to a therapeutic agent (e.g., chemotherapeutic agent or toxin) or an imaging agent (e.g., radioisotope).

A "bispecific antibody" may be produced by recombinant DNA methods in which coding sequences of immunoglobulin genes are manipulated to produce the "bispecific antibody." The coding sequences of the immunoglobulin genes may be used in its entirety, mutated at specific sequences or codons, or used partially by truncating the coding sequences to produce the "bispecific antibody" or components that results in production of a "bispecific antibody."

A "bispecific antibody" includes an intact antibody or a Fv fragment, Fab, Fab' or F(ab')2 fragment coupled chemically, disulphide bridges or by other means to a second determinant which specifically recognizes at least a different target than the target recognized by the intact antibody or the Fv, Fab, Fab' or F(ab )2 fragment. The second determinant includes an second intact antibody different from the binding specificity of the first antibody or the Fv, Fab, Fab' or F(ab')2 fragment of the second antibody.

A "bispecific antibody" of the invention includes antibodies with not only binding specificities for two targets but also include antibodies with additional determinants, which may be derived from immunoglobulin sequences or non-immunoglubulin sequences, with specificities for other target(s).

A "bispecific antibody" includes recombinant variable regions of an immunoglobulin molecule. The F(ab') from two different antibodies may be linked under oxidative condition to form disulphide bonds or may be linked by chemical coupling or through recombinant DNA methods.

A "bispecific antibody" includes chimeric antibodies, recombinant antibodies, humanized antibodies or human antibodies or their derivatives.

A "bispecific antibody" includes antibodies of the invention in which one or more of the complementarity determining region (CDR) of the invention is used to screen for additional antibodies or agents that can compete with the binding of the 3E10, 3G5 or PAb421 antibodies. Peptide, phage display, cDNA, or chemical libraries may be used for such a screen.

As used herein, "anti-DNA monoclonal antibody 3E10" (also referred to herein as 3E10 antibody or mAb 3E10) refers to an antibody produced by ATCC PTA 2439 or a functional fragment or variant thereof or an antibody having the specificity of mAb 3E10. The full 3E10 antibody has been previously described (Weisbart R H, et al. J Immunol. 1990 144(7): 2653-2658; ATCC Accession No. PTA 2439 hybridoma).

As used herein "recombinant variable regions of immunoglobulin molecules" refers to variable regions of Ig molecules which are produced by molecular biological means. Sequences encoding variable domain of the heavy and light chains may be isolated from T-cells, B-cells, leukemic cells, lymphoma cells, or immunoglobulin gene expressing cells, cloned into expression vector systems, and introduced into a host cell to produce "recombinant variable regions of immunoglobulin molecules." Alternatively, the sequences may be recombinantly produced or obtained from genomic DNA. Recombinant antibodies produced in this manner consists of an antibody or antibody fragment with the antigen binding specificity dependent on the variable region, comprising framework sequences and CDRs. Such recombinant antibodies may be formed from a polypeptide chain containing a variable region from a light chain and a polypeptide chain containing a variable region from a heavy chain or alternatively both the light chain and heavy chain variable regions could be found within a polypeptide in which a linker is used to link by recombinant DNA methods the coding sequences for the two variable chain regions, such as in the case of single chain Fv fragment (scFv).

When "recombinant variable regions of immunoglobulin molecules" are formed from two separate polypeptides, one for the light chain variable region and other for the heavy chain variable region, the recombinant Ig molecules may be an intact antibody as is normally produced by an organism from which the coding sequences were isolated or it could be a fragment. Antibody fragments could be produced either by recombinant DNA methods allowing tailored antibodies not dependent on specific protease cleavage sites or by proteolytic cleavage of the recombinant antibodies such as by IdeS, pepsin, or papain to produce Fab, F(ab') or F(ab')2 fragments. The "recombinant variable regions of immunoglobulin molecules" may include the entire constant region or a portion of the constant region. In addition, the constant region of one antibody may be replaced by recombinant DNA method with the constant region of a different antibody if desired.

"Single-chain antibodies" or "Fv" consist of an antibody light chain variable domain or region ("$V_L$") and heavy chain variable region ("$V_H$") connected by a short peptide linker. The peptide linker allows the structure to assume a conformation which is capable of binding to antigen [Bird et al., (1988) Science 242:423 and Huston et al. (1988) Proc. Natl. Acad. Sci. USA 85:5879].

As used herein, a "conservative amino acid substitution" is the replacement of one amino acid with another of a similar type such that the binding specificity of the antibody is preserved. Amino acids of a similar type can be classified into several groups in which one amino acid within a group may be able to substitute for another member of the group:

(1) non-polar aliphatic amino acids, such as alanine, glycine, isoleucine, leucine and valine with alanine and glycine more related to each other and isoleucine, leucine and valine more related to each other based on size;
(2) neutral polar amino acids, such as serine, cysteine, threonine, glutamine and asparagines, and to a lesser extent methionine;
(3) cyclic amino acid, such as proline;
(4) aromatic amino acids, such as phenylalanine, tyrosine, and tryptophan;
(5) basic amino acids, such as histidine, lysine and arginine;
(6) acidic amino acids, such as aspartic acid, glutamic acid, asparagine and glutamine;
(7) aspartic acid and asparagines;
(8) glutamic acid and glutamine; and
(9) alanine, glycine, serine and cysteine Discussions of conservative amino acid substitution may be found in the patent literature as well as in U.S. Pat. Nos. 5,264,558 and 7,700,544.

Moreover, the present invention includes nucleic acids with "silent mutation" or "silent mutations." A silent mutation is a mutation in the DNA which does not result in a change to the amino acid sequence of a protein or results in a change to the amino acid sequence of a protein but not its functionality. Degeneracy of the genetic code allows multiple codons to code for the same amino acid, allowing silent mutations to occur without changing the protein sequence. Such silent mutations are well-known and may be recited readily from publically available and accepted codon tables. In the case of silent mutations in which the amino acid sequence is changed but not the function of the protein, such silent mutations are generally mutations in which one amino acid of a certain chemical/physical characteristics is substituted with another of a similar type. Such mutations may involve conservative amino acid substitutions and may be detected through evolutionary changes but is best determine empirically.

Administration is preferably by methods including, but not limited to, intramuscular injection, subcutaneous injection, nasal spray and other mucosal delivery, intradermal injection with electroporation, electroincorporation, ultrasound, jet injector, and topical patches.

According to the present invention, where administration includes a pharmaceutical formulation, preferably the formulation is a unit dosage containing a daily dose or unit, daily sub-dose or an appropriate fraction thereof, of the active ingredient.

The compositions of the invention can be administered by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, compositions of the invention may be administered alone but may generally be administered in admixture with a suitable pharmaceutical excipient diluent or carrier selected with regard to the intended route of administration and standard pharmaceutical practice.

In embodiments of the present invention in which polypeptides or polynucleotides of the invention are administered parenterally, such administration can be, for example, intravenously, intra-arterially, intraperitoneally, intrathecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Methods of the Invention

The invention provides a method for inhibiting an intracellular target in a cell with a bispecific antibody comprising contacting the cell with a bispecific antibody having a first recombinant variable region of an immunoglobulin molecule with a cell-penetrating determinant (e.g. Fv fragment of mAb 3E10). Preferably the first recombinant variable region causes the bispecific antibody to enter the cell. Additionally, the bispecific antibody has a second recombinant variable region of an immunoglobulin molecule with an intracellular target-binding determinant (e.g. Fv fragment of mAb 3G5) under suitable conditions so that it binds the intracellular target in the cell so that the bispecific antibody inhibits the intracellular target.

In one embodiment, the bispecific antibody is a chimeric, human or humanized antibody. In another embodiment, the bispecific antibody comprises a chimeric, human or humanized bispecific single-chain Fv fragment.

In one embodiment, the first recombinant variable region with a cell-penetrating determinant (e.g. Fv fragment of mAb 3E10) is derived from an anti-DNA antibody. The anti-DNA antibody may be a monoclonal antibody. In one embodiment, the monoclonal antibody is a mAb 3E10 or an antibody that competes with monoclonal antibody 3E10 and is internalizing.

In another embodiment, the first recombinant variable region with a cell-penetrating determinant (e.g. Fv fragment of mAb 3E10) is derived from an antibody transported into a cell through a salvage pathway. The salvage pathway may be a nucleoside salvage pathway which may be mediated by equilibrative nucleoside transporters (ENTs) or SLC29 family of integral membrane proteins. The equilibrative nucleoside transporter (ENT) or a member of the SLC29 family of integral membrane proteins may be a transporter for purine and pyrimidine nucleosides and nucleobases or a metabolite thereof. Further, the transporter for purine and pyrimidine nucleosides and nucleobases or a metabolite thereof may be a human equilibrative nucleoside transporter ENT2.

In yet another embodiment, the antibody transported into a cell through a salvage pathway may be a monoclonal antibody.

In one embodiment, the first Fv fragment comprises one or more complementarity determining regions (CDRs) of mAb 3E10, as specified in SEQ ID NOS:5, 7, 9, 11, 13, and 15.

In another embodiment, the first Fv fragment comprises a CDR with at least 50% amino acid sequence identity or homology to SEQ ID NOS: 5, 7, 9, 11, 13, or 15.

In another embodiment, the first recombinant variable region with a cell-penetrating determinant (e.g. Fv fragment) comprises an anti-DNA monoclonal antibody 3E10 idiotype or an idiotype that competes with monoclonal antibody 3E10 and is internalizing.

In one embodiment, the bispecific antibody is a chimeric, human or humanized antibody that competes with anti-DNA monoclonal antibody 3E10. The antibody that competes with monoclonal antibody 3E10 may be a chimeric, human or humanized antibody that competes with the uptake of anti-DNA monoclonal antibody 3E10 into a cell.

In another embodiment, the uptake of anti-DNA monoclonal antibody 3E10 into a cell is through the equilibrative nucleoside transporter (ENTs) or a member of the SLC29 family of integral membrane proteins expressed by the cell. The equilibrative nucleoside transporter (ENTs) or a member of the SLC29 family of integral membrane proteins is human ENT2.

In one embodiment, the cell with a bispecific antibody is from a mammal. Mammals may include but are not limited to mouse, rat, hamster, cat, dog, rabbit, bovine, pig, sheep, goat, horse, monkey and human.

In one embodiment, the second recombinant variable region with an intracellular target-binding determinant (e.g. Fv fragment of mAb 3G5 or mAb PAb421) is derived from an antibody directed against a cytosolic, nuclear, mitochondrial, endoplasmic reticulum, membrane, and/or organelle macromolecule.

In another embodiment, the second recombinant variable region with an intracellular target-binding determinant (e.g. Fv fragment of mAb 3G5 or mAb PAb421) is derived from an anti-idiotypic antibody directed against an idiotope, a set of idiotopes or an idiotype of an antibody directed against cytosolic, nuclear, mitochondrial, endoplasmic reticulum, membrane, and/or organelle macromolecule. The macromolecule may be a protein, lipid, DNA, or RNA. Further, the protein, lipid, DNA, or RNA macromolecule is modified with a carbohydrate, phosphate group, carboxylic acid group, methyl group, sulfate group, lipid, hydroxyl group, amide group, amino acid, modified amino acid, selenium, ubiquitin, or SUMO protein, or contains a modified base or oxidized base, and combinations thereof.

In yet another embodiment, the macromolecule is a human protein associated with control of cell growth and proliferation, cell cycle, DNA repair, DNA integrity, transcription, replication, translation, or intracellular transport. Examples of protein include but are not limited to Mdm2, BRCA1, MDC1, 53BP1, p53, ATM, ATR, CHK1, CHK2, WT1 (Dao, T. et al., *Sci Transl Med*, 2013, 5(176): 176ra33) or p21.

In another embodiment, the second recombinant variable region with an intracellular target-binding determinant (e.g. Fv fragment) is derived from an anti-oncoprotein antibody or an anti-idiotypic antibody of an anti-oncoprotein antibody. In one embodiment, the anti-oncoprotein antibody or the anti-idiotypic antibody may be a monoclonal antibody and the monoclonal antibody may be directed to the Mdm2 oncoprotein (e.g. mAb 3G5). In an embodiment, the monoclonal antibody is directed to the WT1 oncoprotein (e.g., mAb ESK1).

In another embodiment, the monoclonal antibody is directed to a binding partner of a tumor suppressor protein. In one embodiment, the binding partner of a tumor suppressor protein is Mdm2 oncoprotein. In another embodiment, the tumor suppressor protein is p53 protein.

In one embodiment, the monoclonal antibody is directed to an E3 ubiquitin ligase. In another embodiment, the monoclonal antibody disrupts the binding of an oncoprotein to a tumor suppressor protein. The binding of an oncoprotein to a tumor suppressor protein is the binding of Mdm2 to p53, respectively.

In one embodiment, the bispecific antibody is largely degraded within 4 hours.

The invention also provides a method for increasing p53 tumor suppressor protein levels in a tumor or cancer cell by exposing the cancer cell with a bispecific antibody having a first recombinant variable region with a cell-penetrating determinant (e.g. Fv fragment of mAb 3E10) and a second recombinant variable region with an intracellular target-binding determinant (e.g. Fv fragment of mAb 3G5), thereby increasing the level of p53 tumor suppressor protein levels in a tumor or cancer cell.

In one embodiment, the tumor or cancer is a melanoma, soft tissue tumors, sarcomas, Ewing's sarcoma, leiomyosarcomas, lipomas, liposarcomas, malignant fibrous histiocytomas, malignant Schwannomas, rhabdomyosarcomas, osteosarcomas, brain tumors, central nervous system gliomas, neuroblastoma, glioblastomas, astrocytomas, oligodendrogliomas, soft tissue sarcomas, osteosarcomas, breast cancer, cervical carcinomas, ovarian carcinomas, testicular tumors, urothelial carcinomas, esophageal carcinomas, lung cancers, non-small cell lung carcinoma (NSCLC), nasopharyngeal carcinomas, colorectal cancer, or colon cancer.

The invention further provides a method for inhibiting the growth of tumor or cancer cells in a subject by exposing the tumor or cancer cell to a bispecific antibody of the invention.

The invention also provides a method for inhibiting the growth of MDM2-addicted tumor or cancer cells in a subject by exposing the tumor or cancer cell to a bispecific antibody comprising a first recombinant variable region with a cell-penetrating determinant (e.g. Fv fragment) of anti-DNA monoclonal antibody 3E10 and a second recombinant variable region with an intracellular target-binding determinant for MDM2 (e.g. Fv fragment of mAb 3G5), thereby inhibiting the growth of tumor or cancer cells in the subject. In one embodiment, the tumor or cancer is a melanoma, colon adenocarcinoma, colorectal cancer, glioblastoma or astrocytoma.

The invention further provides a method for regulating activity of MDM2-interacting proteins with a bispecific antibody comprising contacting a cell with a bispecific antibody having a Fv fragment with a cell-penetrating determinant and a second Fv fragment with a binding determinant for MDM2.

In accordance with the invention, the MDM2-interacting proteins may comprise one or more of ABL1, APEX1, AR, ARF/P14, ARRB1, ARRB2, ATM, c-abl, CCNG1, CDKN2AIP, CK2, CTBP1, CTBP2, DAXX, DHFR, DNA pol. ε, DYRK2, E2F/DP1, E1A-associated protein EP300, FKBP3, ERBB4, FOXO4, GLN3, HDAC1, HIF-1α, HIV-1 Tat, HTATIP, IGF1R, L5/RNA, L11, MDM4, MTBP, Numb, p16, p53/TP53, P63, p73/TP73, p300/CBP, PCAF, PI3K/AKT, PML, PSMA3PSMD10, PSME3, PYHIN1, RB, RB1, RBBP6, RBL5, RFWD3, RNA, RP11, RPL5, RPL11, RPL26, RRM2B, RYBP, Sp1, Sumo1, TAFII250, TBGR1, TBP/TFIIE, TRIM13, TRIM28, Tsg101, UBC, UBXN6, USP2, USP7, and human homologs.

In one embodiment, the bispecific antibody comprises bispecific single-chain Fv fragments derived from cell-penetrating monoclonal antibody, mAb 3E10, and anti-MDM2 monoclonal antibody, mAb 3G5.

In another embodiment, the bispecific antibody is a recombinant antibody, chimeric antibody, humanized antibody, or human antibody, or derivatives thereof.

The invention further provides a method for increasing therapeutic effectiveness of treating tumor, cancer or a dis-regulated intracellular process comprising the use of combination therapy with a bispecific antibody comprising: (a) a recombinant variable region with a cell-penetrating determinant (e.g. Fv fragment of mAb 3E10) and a second recombinant variable region with an intracellular target-binding determinant (e.g. Fv fragment of mAb 3G5), and (b) a second bispecific antibody comprising a recombinant variable region with a cell-penetrating determinant (e.g. Fv fragment of mAb 3E10) and an additional second recombinant variable region with an intracellular target-binding determinant (e.g. Fv fragment of mAb PAb421) for a second protein of the same biochemical pathway, intracellular signaling pathway, or regulatory network.

In one embodiment, the Fv fragment with a cell-penetrating determinant is derived from an antibody transported into a cell through a salvage pathway or derived from an anti-DNA antibody. The second Fv fragment with an intracellular target-binding determinant is derived from an anti-oncoprotein antibody. Further, the additional second Fv fragment is derived from a monoclonal antibody directed to the C-terminus of p53 tumor suppressor protein with ability to restore DNA-binding capability of the mutant p53 protein.

In one embodiment, the antibody transported into the cell through a salvage pathway or the antibody derived from an anti-DNA antibody is mAb 3E10. In another embodiment, the antibody derived from an anti-oncoprotein antibody is mAb 3G5.

In another embodiment, the monoclonal antibody directed to the C-terminus of p53 tumor suppressor protein is PAb421 (EMD Millipore catalog Number OP03).

In one embodiment, the bispecific antibody has amino acid sequence of SEQ ID NO:2. In another embodiment, the bispecific antibody is encoded by nucleic acid sequence, as shown in SEQ ID NO:1. In another embodiment, the bispecific antibody comprises one or more of amino acid sequence of SEQ ID NOS:3, 5, 7, 9, 11, 13, 15, 17, 19, 21, 23, 25, or 27. In yet another embodiment, the bispecific antibody is encoded by a nucleic acid sequence, comprising nucleic acid sequence as shown in SEQ ID NO:1 from nucleotide position 268 to 1833, or SEQ ID NOS:4, 6, 8, 10, 12, 14, 16, 18, 20, 22, 24, or 26.

In one embodiment, the bispecific antibody additionally comprises conservative amino acid substitution or substitutions.

In another embodiment, the nucleic acid sequence additionally comprises silent mutation or mutations.

In another embodiment, the bispecific antibody is encoded by a nucleic acid sequence, comprising a nucleic acid sequence of SEQ ID NO:1, SEQ ID NO:1 from nucleotide position 268 to 1833, or SEQ ID NOS: 4, 6, 8, 10, 12, 14, 16, 18, 20, 22, 24, or 26 with one or more conservative amino acid substitution(s) and/or silent mutation(s).

In one embodiment, the second bispecific antibody has amino acid sequence of SEQ ID NO:29. In another embodiment, the second bispecific antibody is encoded by nucleic acid sequence, as shown in SEQ ID NO:28. In another embodiment, the second bispecific antibody comprises one or more of amino acid sequence of SEQ ID NOS:30, 5, 7, 9, 11, 13, 15, 32, 34, 36, 38, 40, or 42. In yet another embodiment, the second bispecific antibody is encoded by a nucleic acid sequence, comprising nucleic acid sequence as shown in SEQ ID NO:28 from nucleotide position 268 to 1827, or SEQ ID NOS:4, 6, 8, 10, 12, 14, 31, 33, 35, 37, 39, or 41.

In one embodiment, the bispecific antibody additionally comprises conservative amino acid substitution or substitutions.

In one embodiment, the nucleic acid sequence additionally comprises silent mutation or mutations.

In one embodiment, the bispecific antibody is encoded by a nucleic acid sequence, comprising a nucleic acid sequence of SEQ ID NO:28, SEQ ID NO:28 from nucleotide position 268 to 1827, or SEQ ID NOS:4, 6, 8, 10, 12, 14, 31, 33, 35, 37, 39, or 41 with one or more conservative amino acid substitution(s) and/or silent mutation(s).

The invention also provides a method for producing a bispecific antibody comprising culturing the host vector system under suitable culture conditions so as to produce the bispecific antibody in the host and recovering the bispecific antibody so produced.

Compositions of the Invention

The invention provides a bispecific antibody comprising a first recombinant variable region of an immunoglobulin molecule with a cell-penetrating determinant (e.g., Fv fragment) from an anti-DNA monoclonal antibody 3E10 or a variable region of an immunoglobulin or polypeptide which competes with monoclonal antibody 3E10. The bispecific antibody further comprises a second recombinant variable region of an immunoglobulin molecule with an intracellular target-binding determinant (e.g., Fv fragment of mAb 3G5) that inhibits the biological activity, biochemical activity, regulatory activity or cellular signal associated with the determinant or a macromolecule to which the determinant is attached. The determinant or macromolecule may be human.

The bispecific antibody may be a chimeric antibody, a recombinant antibody, an anti-idiotypic antibody, a humanized antibody, or an affinity matured antibody. In other embodiments, the antibody fragment is a single domain antibody, a diabody, an scfv, an scfv dimer, a dsfv, a (dsfv)$_2$, a dsFv-dsfv', a bispecific ds diabody, a Fv, a Fab, a Fab', or a F(ab')$_2$. In other embodiments, the antibody fragment may be operably attached to a constant region, e.g. wherein the constant region may be a kappa light chain, gamma-1 heavy chain, gamma-2 heavy chain, gamma-3 heavy chain or gamma-4 heavy chain.

In further embodiments of the aspects of the invention, the isolated or bispecific antibody is a monoclonal antibody.

In one embodiment, the first antibody (e.g. Fv) fragment comprises one or more complementarity determining regions (CDRs) of mAb 3E10, as specified in SEQ ID NOS:5, 7, 9, 11, 13, and 15.

In another embodiment, the bispecific antibody comprises a CDR with at least 50% amino acid sequence identity or homology to SEQ ID NOS:5, 7, 9, 11, 13, or 15.

In another embodiment, the first antibody (e.g. Fv) fragment with a cell-penetrating determinant has monoclonal antibody 3E10 idiotype.

In yet another embodiment, the antibody that competes with the monoclonal antibody 3E10 is a chimeric, human or humanized antibody that competes with the uptake of monoclonal antibody 3E10 into the cell. In one embodiment, the uptake of monoclonal antibody 3E10 into the cell is through an equilibrative nucleoside transporter (ENTs) or a member of the SLC29 family of integral membrane proteins expressed by the cell. In another embodiment, the equilibrative nucleoside transporter (ENTs) or a member of the SLC29 family of integral membrane proteins is ENT2.

In one embodiment, the second antibody (e.g. Fv) fragment with an intracellular target-binding determinant is derived from an anti-idiotypic antibody directed against an idiotope, a set of idiotopes or an idiotype of an antibody directed against a human cytosolic, nuclear, mitochondrial, endoplasmic reticulum, membrane, and/or organelle macromolecule.

In one embodiment, the second antibody (e.g. Fv) fragment with an intracellular target-binding determinant is derived from an antibody directed against a cytosolic, nuclear, mitochondrial, endoplasmic reticulum, membrane, and/or organelle macromolecule.

In another embodiment, the macromolecule is a human protein, DNA, lipid, or RNA. The protein, lipid, DNA, or RNA macromolecule may be modified with a carbohydrate, phosphate group, carboxylic acid group, methyl group, sulfate group, lipid, hydroxyl group, amide group, amino acid, modified amino acid, selenium, ubiquitin, or SUMO protein, or contains a modified base or oxidized base, and combinations thereof.

In one embodiment, the macromolecule is a human protein associated with control of cell growth and proliferation, cell cycle, DNA repair, DNA integrity, transcription, replication, translation, or intracellular transport. In accordance with the invention, the protein may be Mdm2, BRCA1, MDC1, 53BP1, p53, ATM, ATR, CHK1, CHK2, WT1 (Dao, T. et al., Sci Transl Med, 2013, 5(176): 176ra33) or p21.

In one embodiment, the Fv fragment with an intracellular target-binding determinant is derived from an anti-oncoprotein antibody. In another embodiment, the anti-oncoprotein antibody is directed to the Mdm2 oncoprotein. In a further embodiment, the anti-oncoprotein antibody directed to the Mdm2 oncoprotein is a mAb 3G5. In another embodiment, the monoclonal antibody is directed to the WT1 oncoprotein. In a further embodiment, the monoclonal antibody directed to the WT1 oncoprotein is a mAb ESK1.

In one embodiment, the anti-oncoprotein antibody is directed to a binding partner of a tumor suppressor protein. The binding partner of a tumor suppressor may be Mdm2 oncoprotein. Further, the tumor suppressor protein may be a p53 protein.

In one embodiment, the anti-oncoprotein antibody is directed to an E3 ubiquitin ligase.

In another embodiment, the anti-oncoprotein antibody disrupts the binding of an oncoprotein to a tumor suppressor protein.

The binding of an oncoprotein to a tumor suppressor protein may include the binding of Mdm2 to p53.

In another embodiment, the bispecific antibody further comprises a constant region. In one embodiment, the constant region is a kappa light chain, gamma-1 heavy chain, gamma-2 heavy chain, gamma-3 heavy chain or gamma-4 heavy chain.

In another embodiment, the bispecific antibody is produced as a recombinant protein in a bacterial cell, yeast cell, Chinese hamster ovary (CHO) cell, insect cell, or transgenic animals. The yeast cell may be *Pichia pastoris*, e.g., a X-33 cell. In one embodiment, the recombinant protein is secreted and post-translationally modified. In another embodiment, the post-translational modification comprises glycosylation, proteolytic processing of signal sequences, disulfide bridge formation, and/or lipid addition.

In one embodiment, the bispecific antibody comprises one or more amino acid sequence comprising Ala-Gly-Ile-His (AGIH) at the amino terminus of one or both of the recombinant variable region of the immunoglobulin molecule with a cell-penetrating determinant (e.g., a scFv fragment of mAb 3E10).

In one embodiment, the bispecific antibody has amino acid sequence of SEQ ID NO:2. In another embodiment, the bispecific antibody is encoded by nucleic acid sequence, as shown in SEQ ID NO:1. In another embodiment, the bispecific antibody comprises one or more of amino acid sequence of SEQ ID NOS:3, 5, 7, 9, 11, 13, 15, 17, 19, 21, 23, 25, or 27. In yet another embodiment, the bispecific antibody is encoded by a nucleic acid sequence, comprising nucleic acid sequence as shown in SEQ ID NO:1 from nucleotide position 268 to 1833, or SEQ ID NOS:4, 6, 8, 10, 12, 14, 16, 18, 20, 22, 24, or 26.

In one embodiment, the bispecific antibody additionally comprises conservative amino acid substitution or substitutions. In another embodiment, the nucleic acid sequence additionally comprises silent mutation or mutations. In yet another embodiment, the bispecific antibody is encoded by a nucleic acid sequence, comprising a nucleic acid sequence of SEQ ID NO:1, SEQ ID NO:1 from nucleotide position 268 to 1833, or SEQ ID NOS: 4, 6, 8, 10, 12, 14, 16, 18, 20, 22, 24, or 26 with one or more conservative amino acid substitution(s) and/or silent mutation(s).

In one embodiment, the bispecific antibody have the amino acid sequence of SEQ ID NO:29. In another embodiment, the bispecific antibody may be encoded by nucleic acid sequence, as shown in SEQ ID NO:28. In another embodiment, the bispecific antibody comprising one or more of amino acid sequence of SEQ ID NOS:30, 5, 7, 9, 11, 13, 15, 32, 34, 36, 38, 40, or 42. In yet another embodiment, the bispecific antibody encoded by a nucleic acid sequence, comprising nucleic acid sequence as shown in SEQ ID NO:28 from nucleotide position 268 to 1827, or SEQ ID NOS:4, 6, 8, 10, 12, 14, 31, 33, 35, 37, 39, or 41.

In one embodiment, the bispecific antibody additionally comprises conservative amino acid substitution or substitutions. In another embodiment, the nucleic acid sequence additionally comprises silent mutation or mutations. In another embodiment, the bispecific antibody is encoded by a nucleic acid sequence, comprising a nucleic acid sequence of SEQ ID NO:28, SEQ ID NO:28 from nucleotide position 268 to 1827, or SEQ ID NOS:4, 6, 8, 10, 12, 14, 31, 33, 35, 37, 39, or 41 with one or more conservative amino acid substitution(s) and/or silent mutation(s).

The invention further provides for a bispecific antibody or a single chain antibody comprising one or more of gly-gly-gly-gly-serine repeat(s), human CH1 linker, and a swivel sequence.

In one embodiment, the gly-gly-gly-gly-serine repeat(s) are three repeats of gly-gly-gly-gly-serine. In another embodiment, the human CH1 linker comprises the amino acid sequence as provided in SEQ ID NO:3 from amino acid position 253 to 265 or conservative amino acid substitution(s) within the sequence as provided in SEQ ID NO:3 from amino acid position 253 to 265. In one embodiment, the swivel sequence comprises the amino acid sequence as provided in SEQ ID NO:3 from amino acid position 266 to 271.

In one embodiment, the human CH1 linker is linked to the amino terminus of the swivel sequence by a peptide bond. In another embodiment, the human CH1 linker is covalently attached through its amino terminus to the carboxyl end of a Fv fragment.

In one embodiment, the nucleic acid molecule encodes the bispecific antibody of the invention. In another embodiment, the nucleic acid molecule is a DNA (e.g., cDNA) encoding the bispecific antibody of the invention.

The invention also provides for a vector which comprises the nucleic acid molecule of the invention. The host vector system comprises a vector of the invention in a suitable host cell. Examples of suitable host cells include but are not limited to bacterial cell and eukaryotic cell.

The invention also provides for a pharmaceutical composition for treating a subject suffering from tumor, cancer or a dis-regulated intracellular process comprising a bispecific antibody of the invention.

The invention further provides for a pharmaceutical composition for treating a subject suffering from tumor, cancer or a dis-regulated intracellular process comprising a bispecific antibody of the invention.

Examples of tumor or cancer include but are not limited to a melanoma, soft tissue tumors, sarcomas, Ewing's sarcoma, leiomyosarcomas, lipomas, liposarcomas, malignant fibrous histiocytomas, malignant Schwannomas, rhabdomyosarcomas, osteosarcomas, brain tumors, central nervous system gliomas, neuroblastoma, glioblastomas, astrocytomas, oligodendrogliomas, soft tissue sarcomas, osteosarcomas, breast cancer, cervical carcinomas, ovarian carcinomas, testicular tumors, urothelial carcinomas, esophageal carcinomas, lung cancers, non-small cell lung carcinoma (NSCLC), nasopharyngeal carcinomas, colorectal cancer, or colon cancer.

In another aspect, the invention contemplates a pharmaceutical composition comprising the bispecific antibodies of the invention in association with a pharmaceutically acceptable carrier. The pharmaceutical compositions preferably include suitable carriers and adjuvants which include any material which when combined with the molecule of the invention retains the molecule's activity and is non-reactive with the subject's immune system. These carriers and adjuvants include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, phosphate buffered saline solution, water, emulsions (e.g. oil/water emulsion), salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances and polyethylene glycol. Other carriers may also include sterile solutions; tablets, including coated tablets and capsules. Typically such carriers contain excipients such as starch, milk, sugar (e.g. sucrose, glucose, maltose), certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods. Such compositions may also be formulated within various lipid compositions, such as, for example, liposomes as well as in various polymeric compositions, such as polymer microspheres.

In a further embodiment, the bispecific antibody is conjugated to the chemotherapeutic agent, a toxin, a radioisotope, or a detectable label.

In another embodiment, the invention provides an article of manufacture comprising a container and a composition of the invention contained therein.

In embodiments of the articles of manufacture of the invention, the article of manufacture comprises a bispecific antibody of the invention or antigen-binding fragment thereof operably attached to a chemotherapeutic agent, a toxin, a radioisotope.

In one embodiment, the compositions of the invention further comprises a therapeutic agent admixed with the bispecific antibody. The therapeutic agent may be an anti-cancer agent which may be lenalidomide, ipilimumab, rituximab, alemtuzumab, ofatumumab, flavopiridol, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; amino glutethimide; amsacrine; anastrozole; anthramycin; asparaginase; asperlin; azacitidine; azetepa; azotomycin; batimastat; benzodepa; bicalutamide; bisantrene hydrochloride; bizelesin; bleomycin sulfate; brequinar sodium; bropirimine; busulfan; cactinomycin; calusterone; caracemide; carbetimer; carboplatin; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfmer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogeranium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfm; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

In another embodiment, the compositions of the invention further comprising a therapeutic agent admixed with the bispecific antibody and the therapeutic agent may be an alkylating agent which includes but are not limited to nitrogen mustards (e.g., bendamustine, mechloroethamine, cyclophosphamide, chlorambucil, melphalan), ethylenimine and methylmelamines (e.g., hexamethlymelamine, thiotepa), alkyl sulfonates (e.g., busulfan), nitrosoureas (e.g., carmustine, lomustine, semustine, streptozocin), or triazenes (decarbazine).

Kits of the Invention

According to another aspect of the invention, kits are provided. Kits according to the invention include package(s) comprising composition of the invention.

The phrase "package" means any vessel containing compositions presented herein. In preferred embodiments, the package can be a box or wrapping. Packaging materials for use in packaging pharmaceutical products are well known to those of skill in the art. Examples of pharmaceutical packaging materials include, but are not limited to, blister packs, bottles, tubes, inhalers, pumps, bags, vials, containers, syringes (including pre-filled syringes), bottles, and any packaging material suitable for a selected formulation and intended mode of administration and treatment.

The kit can also contain items that are not contained within the package but are attached to the outside of the package, for example, pipettes.

Kits may optionally contain instructions for administering compositions of the present invention to a subject having a condition in need of treatment. Kits may also comprise instructions for approved uses of components of the composition herein by regulatory agencies, such as the United States Food and Drug Administration. Kits may optionally contain labeling or product inserts for the present compositions. The package(s) and/or any product insert(s) may themselves be approved by regulatory agencies. The kits can include compositions in the solid phase or in a liquid phase (such as buffers provided) in a package. The kits also can include buffers for preparing solutions for conducting the methods, and pipettes for transferring liquids from one container to another.

The kit may optionally also contain one or more other compositions for use in therapies as described herein. In certain embodiments, the package(s) is a container for intravenous administration.

The following examples are presented to illustrate the present invention and to assist one of ordinary skill in making and using the same. The examples are not intended in any way to otherwise limit the scope of the invention.

EXAMPLES

Example 1

Materials and Methods
Cell lines

Cell lines obtained from the American Type Culture Collection (ATCC) include: COS-7 monkey kidney cells; MC-7 human ovarian cancer cells that over-express MDM2; 3T3 transformed mouse fibroblasts; BJ primary human fibroblasts. Human melanoma cells sensitive to MDM2 inhibition were obtained from Maria S. Soengas, Madrid, Spain, and included SK-MEL-103, SK-MEL-147, UACC-62, and UACC-257. These cell lines were not authenticated by our laboratory after receiving them.

Design, Expression, and Purification of the 3E10-3G5 Bispecific Antibody

3G5 hybridoma was obtained from Arnold J. Levine, Princeton University. 3G5 Vk and VH were cloned by RT-PCR from hybridoma RNA with degenerate primers designed to identify mouse immunoglobulin variable region genes, and 3G5 scFv was constructed as described previously (4). Variable region heavy and light chains were attached with a $(GGGGS)_3$ linker. The Fv fragments were connected with a linker composed of CH1 sequences combined with a swivel sequence (6). 3E10-3G5 bispecific scFv cDNA was constructed in pPicZαA (Invitrogen, Carlsbad, CA; Catalog No. V195-20) between the EcoRI and XbaI cloning sites in frame with the C-terminal myc-his$_6$ tag. Plasmids were transfected into X-33 cells, and a high-secreting clone was identified as described previously (6). Bispecific antibody was purified from X-33 supernatant by metal chelation chromatography on Ni-NTA-Agarose. The bispecific antibody was shown to be stable at 4° C. for 3 months.

Cell Penetration Assay

COS-7 cells were incubated with control media, media containing 10 μM 3E10 scFv, or media containing 10 μM 3E10-3G5 for one hour. Media was then removed from the cells, and cells were washed, fixed, and stained with an anti-myc antibody as described previously (3).

In Vitro Assays of 3E10-3G5 Cytotoxicity

Cells were grown in DMEM with 10% FCS. Adherent cells were removed with EDTA and distributed in 96-well plates overnight in the presence of medium alone, 3E10, or 3E10-3G5. Growth was evaluated after 3 days by counting cells. Results were expressed as percent total cell number (relative to control)±S.D.

In Vivo Assays of 3E10-3G5 Cytotoxicity

Animal studies were done under a protocol approved by the Veterans Affairs Institutional Animal Care and Use Committee. Nude mice (nu/nu) were obtained from The Jackson Laboratory, Bar Harbor, Maine. Six Nude mice were injected subcutaneously with $1\times10^6$ UACC-257 cells and observed (control). Six Nude mice were injected subcutaneously with $1\times10^6$ UACC-257 cells on day 1 and treated with intraperitoneal injections of 1.0 mg 3E10-3G5 scFv on days 1 through 4. Tumor volume (mm$^3$) was measured in mice that developed tumors, and animals were euthanized when tumors exceeded 2000 mm$^3$ or at the termination of the experiment on day 22.

Western Blot Assays

UACC-257 tumors were excised, and tumor tissue was lysed in 2% SDS. Protein (20 µg) from each tumor was electrophoresed in a 4-20% polyacrylamide gradient gel and then transblotted to a nylon membrane. Western blots were probed with antibodies to p53, MDM2, and actin.

Statistical Analyses

Significant differences in tumor growth were determined by Students t test.

Results

3E10-3G5 Retains the MDM2-Binding Activity of 3G5 and the Cell-Penetrating Activity of 3E10

A 3E10-3G5 bispecific antibody composed of the single chain variable fragments of the cell-penetrating 3E10 antibody and the anti-MDM2 3G5 antibody was produced as a secreted protein by *Pichia pastoris* X-33 cells transfected with pPicZαA containing the bispecific scFv cDNA (FIG. 1A). 3E10-3G5 was purified from yeast supernatant by metal chelation chromatography on Ni-NTA-Agarose as described previously (6) (FIG. 1B). Purified 3E10-3G5 was used as a probe for MDM2 in a Western blot assay on lysates from MC-7 cells over-expressing MDM2, and was found to recognize and bind MDM2 similar to the full 3G5 antibody and with similar binding specificity (FIG. 1C). MC-7 cells were selected as a convenient source of MDM2. Next, 3E10-3G5 was applied to COS-7 cells in culture and was observed to penetrate into the cells and localize in nuclei similar to 3E10 scFv alone (FIG. 1D). COS-7 cells over-express hENT-2 and served as a convenient model cell to demonstrate cellular penetration by the bispecific scFv. These results demonstrate that the 3E10-3G5 bispecific antibody retains the cell-penetrating activity of 3E10 scFv and the MDM2-binding activity of 3G5 scFv.

3E10-3G5 Impairs the Growth of MDM2-Addicted Melanoma Cells

We next investigated the impact of 3E10-3G5 on melanoma cells known to be sensitive to MDM2 inhibition (10). UACC-257 melanoma cells were incubated for 3 days with media containing concentrations of 3E10-3G5 ranging from 0-10 □M. 3E10 and 3G5 alone were used as controls and had no observable effect on the growth or morphology of UACC-257 melanoma cells compared to culture medium (FIG. 2C). However, 3E10-3G5 delayed the growth of the cells in a dose-responsive manner, with significant growth delay observed at a dose of 10 □M (FIG. 2A). A similar effect was observed in additional MDM2-addicted melanoma cell lines, with marked inhibition of growth and distinct morphological changes observed in all of the melanoma cell lines tested (FIG. 2B and 2C). As expected, 3E10 and 3G5 alone had no apparent effect on any of the melanoma cell lines (FIG. 2). Importantly, 3E10-3G5 had only a mild impact on the growth of murine 3T3 transformed fibroblasts and had no effect on the growth of BJ primary human fibroblasts (FIG. 2B). Taken together these data suggest that 3E10-3G5 successfully inhibited MDM2 in vitro and caused a growth delay specifically in the MDM2-addicted cells.

3E10-3G5 Inhibits Growth of Melanoma Tumors in Vivo

The activity of 3E10-3G5 in vivo was tested in a human melanoma xenograft model. Nude mice were injected subcutaneously with $1\times10^6$ UACC-257 cells, and mice were observed or treated for 4 consecutive days with intraperitoneal injections of 1.0 mg 3E10-3G5 beginning at day 1. Four mice in the control group and five mice in the experimental group developed tumors. Mice that developed tumors were then followed closely and tumor volumes were measured. Importantly, treatment with 3E10-3G5 was not associated with any clinical toxicity, as treated mice were indistinguishable from control mice with respect to their appearance and activity. However, treatment with 3E10-3G5 significantly inhibited tumor growth at day 20 (p=0.041) and at the termination of the experiment on day 22 (p=0.026) (FIG. 3A-3C). In order to probe the mechanism responsible for tumor growth inhibition, we evaluated the relative levels of p53 and MDM2 in representative tumors from three untreated mice and three mice treated with 3E10-3G5. Treatment with 3E10-3G5 increased the expression of MDM2 and p53 as shown in Western blots of tumor lysates probed with antibodies to p53 and MDM2 (FIG. 3D). Actin served as a loading control. These results are similar to changes in MDM2 and p53 levels observed in cells and tumors treated with small molecule inhibitors of MDM2 (10) and further suggest that 3E10-3G5 successfully inhibited MDM2 in vivo.

Discussion

We have demonstrated that treatment with a 3E10-3G5 bispecific antibody impairs the growth of melanoma cells in vitro and in vivo. This growth delay is likely the result of increased levels of activated p53 that have been freed from inhibition by MDM2 by the action of the 3G5 antibody fragment. In keeping with this hypothesis, elevated levels of p53 were observed in tumors in mice treated with the bispecific antibody. We also noted that these tumors exhibited increased levels of MDM2, which is consistent with results obtained by others with MDM2 inhibitors such as Nutlin-3, and is likely the result of increased levels of p53 driving additional production of MDM2 (10). Since MDM2 has numerous p53-independent effects (10) it is possible that the impact of 3E10-3G5 on the melanoma cells and tumors is the result of an effect on diverse metabolic pathways in addition to its impact on p53 function. Although we administered micromolar amounts of 3E10-3G5 to mice, only nanomolar amounts are internalized intracellularly consistent with antigen-binding specific effects.

We previously constructed and demonstrated efficacy of a cell-penetrating bispecific antibody composed of 3E10 scFv and the scFv fragment of mAb PAb421, an antibody that binds and restores the function of some p53 mutants (6). In the present study we have extended our cell-penetrating bispecific antibody technology by demonstrating the effectiveness of this approach in modulating MDM2 activity in vivo. Since p53 activity can be inhibited by mutation and/or over-expression of MDM2, combination therapy with 3E10-3G5 and 3E10-PAb421 may prove particularly useful in select tumor cells.

Our studies establish proof-of-principle for the use of the cell-penetrating antibody 3E10 as a transport vehicle to deliver therapeutic antibody fragments directed to intracellular and intranuclear targets. The exquisite antigen-binding specificity of antibodies delivered into intracellular compartments will likely result in improved therapeutic indices by avoiding off-target binding responsible for toxic side effects of small molecule inhibitors. In addition, cell-penetrating bispecific antibodies can be designed that bind intracellular epitopes such as transcription factors and DNA repair proteins that cannot presently be targeted with small molecule inhibitors and are currently considered undruggable. The use of cell-penetrating bispecific antibodies in targeted molecular therapy will significantly broaden the spectrum of accessible intracellular targets and may have a profound impact in cancer therapy.

Example 2

3E10-PAb421 Inhibits Growth of HT29 Cells in Vitro and in Vivo

Figure 6B:
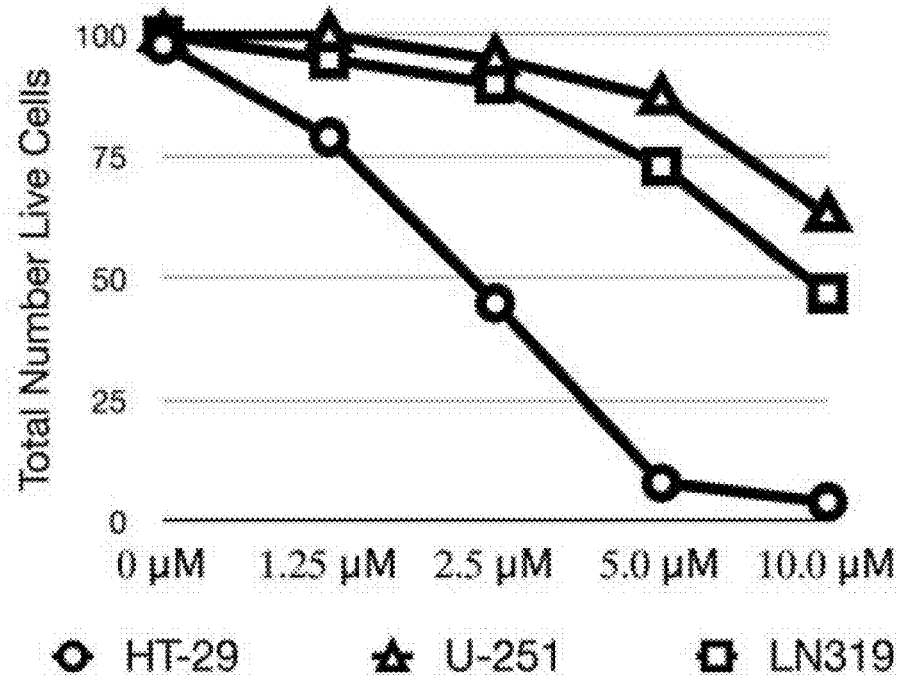
Figure 9A:
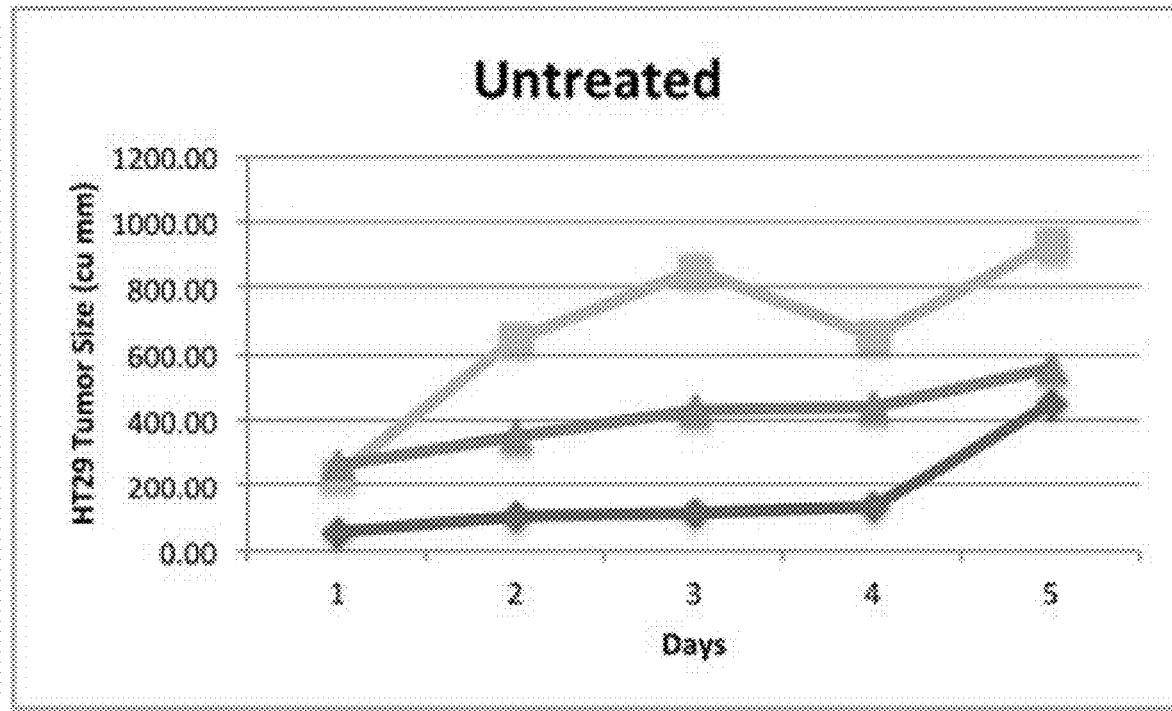
FIGS. 9A-B show line graphs of untreated HT-29 tumor (FIG. 9A) and HT-29 tumor treated with 3E10-PAb421 (FIG. 9B) in vivo in a nude mouse xenograft model.
Figure 9B:
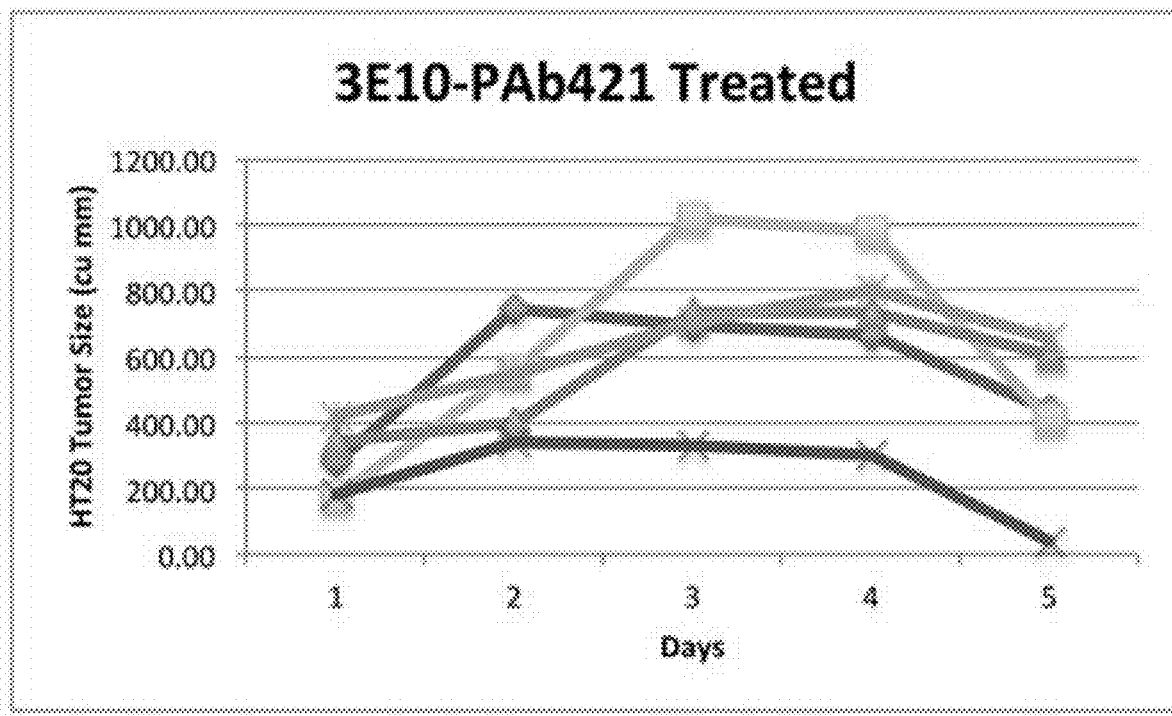

3E10-PAb421 bispecific single-chain antibody was assayed in vitro for cytotoxicity against the colon cancer cell line, HT29 and glioblastoma cell line, U251 both containing p53 mutation R273H. Also tested was the astrocytoma cell line, LN319 containing p53 mutation R175H. All of the cell lines showed dose-response inhibition of growth in response to 3E10-PAb421 (FIG. 6). Moreover, 3E10-PAb421 and 3E10-3G5 were synergistic in inhibiting the growth of cancer cells (FIG. 7). Cytotoxicity in vitro is shown in a photomicrograph (FIG. 8). Nude mice were used to study the effect of 3E10-PAb421 on the growth of HT29 cancer cells in vivo. Mice were injected with $2 \times 10^6$ HT29 cells in the hind flank. When tumors reached 400 mm$^3$, 1.5 mg of 3E10-PAb421 was injected intraperitoneally daily. 3E10-PAb421 inhibited growth of tumors 2 to 3 days following initiation of therapy (FIG. 9).

REFERENCES

1. Zhang J, Yang P L, Gray N S. Targeting cancer with small molecule kinase inhibitors. Nature Reviews Cancer 2009; 9:28-39.
2. Zack D J, Stempniak M, Wong A L, Taylor C, Weisbart R H. Mechanisms of cellular penetration and nuclear localization of an anti-double strand DNA autoantibody. J Immunol 1996; 157:2082-8.
3. Hansen J E, Tse C M, Chan G, Heinze E R, Nishimura R N, Weisbart R H. Intranuclear protein transduction through a nucleoside salvage pathway. J Biol Chem 2007; 282:20790-3.
4. Weisbart R H, Stempniak, M, Harris, S, Zack, D J, Ferreri K. An autoantibody is modified for use as a delivery system to target the cell nucleus: Therapeutic implications. J Autoimmun 1998; 11:539-46.
5. Weisbart R H, Baldwin R, Huh B, Zack D J, Nishimura R. Novel protein transfection of primary rat cortical neurons utilizing an antibody that penetrates living cells. J Immunol 2000; 164:6020-6.
6. Weisbart R H, Wakelin R, Chan G, Miller C W, Koeffler P H. Construction and expression of a bispecific single-chain antibody that penetrates mutant p53 colon cancer cells and binds p53. Int J Onc 2004; 25:1113-8.
7. Hansen J E, Fischer L K, Chan G, Chang S S, Baldwin S W, Aragon R J et al. Antibody-mediated p53 protein therapy prevents liver metastasis in vivo. Cancer Res 2007; 67:1769-74.
8. Heinze E, Baldwin S, Chan G, Hansen J, Song J, Clements D et al. Antibody-mediated FOXP3 protein therapy induces apoptosis in cancer cells in vitro and inhibits metastasis in vivo. Int J Oncol 2009; 35:167-73.
9. Zhan X, Ander BP, Liao I H, Hansen J E, Kim C, Clements D et al. Recombinant Fv-Hsp70 protein mediates neuroprotection after focal cerebral ischemia in rats. Stroke 2010; 3:538-43.
10. Verhaegen M, Checinska A, Riblett M B, Wang S, Soengas M S. E2F1-dependent oncogenic addiction of melanoma cells to MDM2. Oncogene 2012; 7:828-41.
11. Chen J, Marechal V, Levine A J. Mapping of the p53 and mdm-2 Interaction Domains. Mol. & Cell Biol 1993; 13:4107-14.
12. Bottger A, Bottger V, Garcia-Echeverria C, Chene P, Hochkeppel H K, Sampson W et al. Molecular characterization of the hdm2-p53 interaction. 1997; 269: 744-56.
13. Rayburn E, Zhang R, He J, Wang H. MDM2 and Human Malignancies: Expression, Clinical Pathology, Prognostic Markers, and Implications for Chemotherapy. Current Cancer Drug Targets 2005; 5:27-41.
14. Shangary S, Wang S. Small-molecule inhibitors of the MDM2-p53 protein-protein interaction to reactivate p53 function: a novel approach for cancer therapy. Annu Rev Pharmacol Toxicol 2009; 49:223-41.
15. Lane D P, Brown C J, Verma C, Cheok C F. New insights into p53 based therapy. Discovery Med 2011; 63:107-17.

SEQUENCE LISTING

```
Sequence total quantity: 42
SEQ ID NO: 1          moltype = DNA  length = 1905
FEATURE               Location/Qualifiers
misc_feature          1..1905
                      note = Coding sequences for full length unprocessed
                      bispecific scFv3E10-3G5 chimeric antibody derived from Mus
                      musculus, Homosapiens, Saccharomyces cerevisiae, and
                      synthetic sequence from noknown organism
misc_feature          1..3
                      note = ATG, start site of translation provided by
                      pPicZalpha Aexpression vector
misc_feature          1..267
                      note = Coding sequence for Saccharomyces
                      cerevisiaealpha-factorsecretory signal sequence for
                      secretion of fusion protein,provided by pPicZalpha A
                      expression vector
misc_feature          253..258
                      note = Kex2 signal cleavage site between Arg-Glu encoded by
```

|                |                                                                                                                                                                                              |
| -------------- | -------------------------------------------------------------------------------------------------------------------------------------------------------------------------------------------- |
|                | nucleotidepositions 253-258 for removing alpha-factor secretory signal                                                                                                                       |
| misc_feature   | 259..264                                                                                                                                                                                     |
|                | note = Ste13 signal cleavage site between Ala-Glu encoded by nucleotidepositions 259-264 for removing alpha-factor secretory signal                                                          |
| misc_feature   | 265..270                                                                                                                                                                                     |
|                | note = Ste13 signal cleavage site between Ala-Ala encoded by nucleotidepositions 265-270 for removing alpha-factor secretory signal                                                          |
| misc_feature   | 268..279                                                                                                                                                                                     |
|                | note = Ala-Gly-Ile-His peptide coding sequence for increasing solubilityof scFv bispecific antibody                                                                                          |
| misc_feature   | 272..277                                                                                                                                                                                     |
|                | note = EcoRI restriction enzyme site, recreated after insertion of3E10-3G5 scFVc EcoRI-XbaI cDNA fragment into EcoRI-XbaI sites ofpPicZalpha A expression vector                             |
| misc_feature   | 280..1833                                                                                                                                                                                    |
|                | note = 3E10-3G5 bispecific scFv antibody coding sequence with enhancedcell penetration mutation                                                                                              |
| misc_feature   | 280..1023                                                                                                                                                                                    |
|                | note = 3E10 Fv fragment coding sequence with enhanced cell penetrationmutation                                                                                                               |
| misc_feature   | 280..630                                                                                                                                                                                     |
|                | note = anti-DNA monoclonal antibody 3E10 kappa light (Vk) chain codingsequence from Mus musculus                                                                                             |
| misc_feature   | 382..393                                                                                                                                                                                     |
|                | note = 3E10 kappa light (Vk) chain complementarity determining region 1(CDR1) coding sequence from Mus musculus                                                                              |
| misc_feature   | 442..459                                                                                                                                                                                     |
|                | note = 3E10 kappa light (Vk) chain CDR2 coding sequencefrom Musmusculus                                                                                                                      |
| misc_feature   | 556..582                                                                                                                                                                                     |
|                | note = 3E10 kappa light (Vk) chain CDR3 coding sequencefrom Musmusculus                                                                                                                      |
| misc_feature   | 631..675                                                                                                                                                                                     |
|                | note = (GGGGS)3 peptide linker coding sequence                                                                                                                                               |
| misc_feature   | 676..1023                                                                                                                                                                                    |
|                | note = anti-DNA monoclonal antibody 3E10 variable heavy (VH) chaincoding sequence from Mus musculus with enhanced cell penetrationmutation (D31N mutation at CDR1 of VH chain)               |
| misc_feature   | 766..780                                                                                                                                                                                     |
|                | note = 3E10 variable heavy (VH) chain CDR1 coding sequencefrom Musmusculus with D31N mutation for enhanced cell penetration                                                                  |
| misc_feature   | 766..768                                                                                                                                                                                     |
|                | note = Asn amino acid coding sequence; D31N mutation in first amino acidof CDR1 of 3E10 variable heavy (VH) chain for enhanced cellpenetration                                               |
| misc_feature   | 823..873                                                                                                                                                                                     |
|                | note = 3E10 variable heavy (VH) chain CDR2 coding sequencefrom Musmusculus                                                                                                                   |
| misc_feature   | 970..990                                                                                                                                                                                     |
|                | note = 3E10 variable heavy (VH) chain CDR3 coding sequencefrom Musmusculus                                                                                                                   |
| misc_feature   | 1024..1062                                                                                                                                                                                   |
|                | note = Human constant heavy chain 1 (CH1) linker coding sequence                                                                                                                             |
| misc_feature   | 1063..1080                                                                                                                                                                                   |
|                | note = Swivel coding sequence                                                                                                                                                                |
| misc_feature   | 1081..1833                                                                                                                                                                                   |
|                | note = 3G5 Fv fragment coding sequence                                                                                                                                                       |
| misc_feature   | 1081..1419                                                                                                                                                                                   |
|                | note = anti-MDM2 monoclonal antibody 3G5 kappa light (Vk) chain codingsequence from Mus musculus                                                                                             |
| misc_feature   | 1150..1182                                                                                                                                                                                   |
|                | note = 3G5 kappa light (Vk) chain complementarity determining region 1(CDR1) coding sequence from Mus musculus                                                                               |
| misc_feature   | 1228..1248                                                                                                                                                                                   |
|                | note = 3G5 kappa light (Vk) chain CDR2 coding sequence from Mus musculus                                                                                                                     |
| misc_feature   | 1345..1371                                                                                                                                                                                   |
|                | note = 3G5 kappa light (Vk) chain CDR3 coding sequence from Mus musculus                                                                                                                     |
| misc_feature   | 1420..1464                                                                                                                                                                                   |
|                | note = (GGGGS)3 peptide linker coding sequence                                                                                                                                               |

| misc_feature | 1465..1833 |
| | note = anti-MDM2 monoclonal antibody 3G5 variable heavy |
| | (VH) chaincoding sequence from Mus musculus |
| misc_feature | 1555..1569 |
| | note = 3G5 variable heavy (VH) chain CDR1 coding sequence |
| | from Musmusculus |
| misc_feature | 1612..1668 |
| | note = 3G5 variable heavy (VH) chain CDR2 coding sequence |
| | from Musmusculus |
| misc_feature | 1765..1800 |
| | note = 3G5 variable heavy (VH) chain CDR3 coding sequence |
| | from Musmusculus |
| misc_feature | 1836..1841 |
| | note = XbaI restriction enzyme site, recreated after |
| | insertion of3E10-3G5 scFVc EcoRI-XbaI cDNA fragment into |
| | EcoRI-XbaI sites ofpPicZalpha A expression vector |
| misc_feature | 1840..1869 |
| | note = Myc epitope tag, EQKLISEEDL, coding sequence |
| | provided bypPicZalpha A expression vector |
| misc_feature | 1885..1902 |
| | note = (His)6 epitope tag coding sequence, provided by |
| | pPicZalpha Aexpression vector |
| misc_feature | 1903..1905 |
| | note = TGA, stop codon provided by pPicZ A expression vector |
| source | 1..1905 |
| | mol_type = other DNA |
| | organism = synthetic construct |
| CDS | 1..1905 |
| | note = Coding sequences for full length unprocessed |
| | bispecific scFv3E10-3G5 chimeric antibody with secretory |
| | signal, proteasecleavage sites, solubility enhancing |
| | peptide, and epitope tagsproduced using pPicZalpha A |
| | expression vector in Pichia pastoris |

SEQUENCE: 1

```
atgagatttc cttcaattttt tactgctgtt ttattcgcag catcctccgc attagctgct   60
ccagtcaaca ctacaacaga agatgaaacg gcacaaattc cggctgaagc tgtcatcggt  120
tactcagatt tagaagggga tttcgatgtt gctgttttgc catttccaa cagcacaaat   180
aacgggttat tgtttataaa tactactatt gccagcattg ctgctaaaga agaaggggta   240
tctctcgaga aaagagaggc tgaagctgca ggaattcacg acattgtcct gacacagtct   300
cctgcttcct tagctgtatc tctggggcag agggccacca tctcctgcag ggccagcaaa   360
agtgtcagta tctctagcta tagttacatg cactggtacc aacagaaacc aggacagcca   420
cccaaactcc tcatcaagta tgcatcctac ctagaatctg gggttcctgc caggttcagt   480
ggcagtgggt ctgggacaga cttcacccts aacatccatc ctgtggagga ggaggatgct   540
gcaacatatt actgtcagca cagtagggag tttccggtgga cgttcggtgg aggcaccaag   600
ctggaaatca aacgggctga tgctgcaccc ggggtgcg ttctggcgg tggcggttct   660
ggaggcggtg gctctgaggt gcagctggtg gagtctgggg gaggcttagt gaagcctgga   720
gggtccctga aactctcctg tgcagcctct ggattcactt tcagtaacta tggaatgcac   780
tgggtccgtc aggctccaga aaggggggcg gaggtgggttg catacattag tagtggcagt   840
agtaccatct actatgcaga cacagtgaag ggccgattca ccatctccag agacaatgcc   900
aagaacaccc tgttcctgca aatgaccagt ctaaggtctg aggacacagc catgtattac   960
tgtgcaaggc gggggttact acttgactac tggggccaag gcaccactct cacagtctcc  1020
tcagcttcca ccaagggccc atccgtcttc ccctggcgc cctggagtc ttccggatcc  1080
gacatccaga tgactcagtc tccagcctcc ctatctgtat ctgtgggaga aactgtcacc  1140
atcacatgtc gagcaagtga gaatatttac agtaatttag catggtatca gcagaaacag  1200
ggaaaatctc ctcagctcct ggtgtatggt gcaacaaaat tacagatgt tgtgccatca  1260
aggttcagtg gcagtggctc aggcacacag tattccctca agatcaacag cctgcagtct  1320
gaagattttg ggagttatta ctgtcaacat ttttggggta ctcctccgac gttcggtgga  1380
ggcaccaagc tggaactcaa aagggctgat gctgcaccag aggggagg gtctggtggg  1440
ggcggttccg gaggcggagg ctcagaggtg caacttgttg agtctggtgg aggattggtg  1500
cagcctaaag ggtcattgaa actctcatgt gcagcctctg gattccctt caataccac  1560
ggcatgaact gggtccgcca ggctccagga aagggtttgg aatgggtcgg tcgcataaga  1620
actaaaaata tatttatgc aacatattat acgcttcag tgaaagacag gttcaccatt  1680
tccagagatg attcagaaag catgctctat ctgcaaatga caacttgaa aactgaggac  1740
acagccatgt attactgtgt gagacaaggg gacgaattac gggttatgc tctgactac  1800
tggggtcagg gaacctcagt caccgtctcc tcacatctag aacaaaaact catctcagaa  1860
gaggatctga atagcgccgt cgaccatcat catcatcatc attga                  1905
```

| SEQ ID NO: 2 | moltype = AA   length = 634 |
| FEATURE | Location/Qualifiers |
| REGION | 1..634 |
| | note = Synthetic Construct |
| source | 1..634 |
| | mol_type = protein |
| | organism = synthetic construct |

SEQUENCE: 2

```
MRFPSIFTAV LFAASSALAA PVNTTTEDET AQIPAEAVIG YSDLEGDFDV AVLPFSNSTN   60
NGLLFINTTI ASIAAKEEGV SLEKREAEAA GIHDIVLTQS PASLAVSLGQ RATISCRASK  120
SVSTSSYSYM HWYQQKPGQP PKLLIKYASY LESGVPARFS GSGSGTDFTL NIHPVEEEDA  180
ATYYCQHSRE FPWTFGGGTK LEIKRADAAP GGGGSGGGGS GGGGSEVQLV ESGGGLVKPG  240
```

```
GSRKLSCAAS GFTFSNYGMH WVRQAPEKGL EWVAYISSGS STIYYADTVK GRFTISRDNA    300
KNTLFLQMTS LRSEDTAMYY CARRGLLLDY WGQGTTLTVS SASTKGPSVF PLAPLESSGS    360
DIQMTQSPAS LSVSVGETVT ITCRASENIY SNLAWYQQKQ GKSPQLLVYG ATNLADGVPS    420
RFSGSGSGTQ YSLKINSLQS EDFGSYYCQH FWGTPPTFGG GTKLELKRAD AAPGGGGSGG    480
GGSGGGGSEV QLVESGGGLV QPKGSLKLSC AASGFTFNTY GMNWVRQAPG KGLEWVGRIR    540
TKNNIYATYY DASVKDRFTI SRDDSESMLY LQMNNLKTED TAMYYCVRQG DELRGYALDY    600
WGQGTSVTVS SHLEQKLISE EDLNSAVDHH HHHH                                634

SEQ ID NO: 3               moltype = AA   length = 522
FEATURE                    Location/Qualifiers
REGION                     1..522
                           note = Protein sequence for bispecific scFv 3E10-3G5
                               chimeric antibodyderived from Mus musculus, Homo sapiens,
                               and synthetic sequencefrom no known organism with
                               increased solubility peptide butwithout signal sequence or
                               epitope tag.
REGION                     1..4
                           note = MISC_FEATURE - AGIH peptide for increased solubility
REGION                     5..522
                           note = MISC_FEATURE - 3E10-3G5 bispecific scFv chimeric
                               antibody with enhanced cellpenetration mutation but no
                               secretory signal or epitope tag
SITE                       5
                           note = MISC_FEATURE - Start of 3E10 kappa light (Vk) chain
                               from Mus musculus
REGION                     5..252
                           note = MISC_FEATURE - 3E10 Fv fragment with enhanced cell
                               penetration mutation (D31Nmutation at CDR1 of 3E10 VH
                               chain)
REGION                     5..121
                           note = MISC_FEATURE - anti-DNA monoclonal antibody 3E10
                               kappa light (Vk) chainpolypeptide sequence from Mus
                               musculus
REGION                     39..42
                           note = MISC_FEATURE - 3E10 kappa light (Vk) chain
                               complementarity determining region 1(CDR1) amino acid
                               sequence from Mus musculus
REGION                     59..64
                           note = MISC_FEATURE - monoclonal antibody 3E10 kappa light
                               (Vk) chain CDR2 amino acidsequence from Mus musculus
REGION                     97..105
                           note = MISC_FEATURE - 3E10 kappa light (Vk) chain CDR3
                               amino acid sequence from Musmusculus
SITE                       121
                           note = MISC_FEATURE - End of 3E10 kappa light (Vk) chain
                               from Mus musculus
REGION                     122..136
                           note = MISC_FEATURE - (GGGGS)3 peptide linker sequence
REGION                     137..252
                           note = MISC_FEATURE - anti-DNA monoclonal antibody 3E10
                               variable heavy (VH) chainpolypeptide sequence from Mus
                               Musculus with enhanced cellpenetration mutation (D31N
                               mutation at CDR1 of 3E10 VH chain)
SITE                       137
                           note = MISC_FEATURE - Start of 3E10 variable heavy (VH)
                               chain from Mus musculus
REGION                     167..171
                           note = MISC_FEATURE - 3E10 variable heavy (VH) chain CDR1
                               amino acid sequence from Musmusculus with D31N mutation
                               for enhanced cell penetration
SITE                       167
                           note = MISC_FEATURE - Asn amino acid; D31N mutation in CDR1
                               of 3E10 variable heavy (VH)chain for enhanced cell
                               penetration
REGION                     186..202
                           note = MISC_FEATURE - 3E10 variable heavy (VH) chain CDR2
                               amino acid sequence from Musmusculus
REGION                     235..241
                           note = MISC_FEATURE - 3E10 variable heavy (VH) chain CDR3
                               amino acid sequence from Musmusculus
SITE                       252
                           note = MISC_FEATURE - End of 3E10 variable heavy (VH) chain
                               from Mus musculus
REGION                     253..265
                           note = MISC_FEATURE - Human constant heavy chain 1 (CH1)
                               linker sequence
REGION                     266..271
                           note = MISC_FEATURE - Swivel sequence
REGION                     272..522
```

|  |  |
|---|---|
| REGION | 272..384<br>note = MISC_FEATURE - 3G5 Fv fragment polypeptide sequence<br>note = MISC_FEATURE - anti-MDM2 monoclonal antibody 3G5 kappa light (Vk) chainpolypeptide sequence from Mus musculus |
| SITE | 272<br>note = MISC_FEATURE - Start of 3G5 kappa light (Vk) chain from Mus musculus |
| REGION | 295..305<br>note = MISC_FEATURE - 3G5 kappa light (Vk) chain complementarity determining region 1(CDR1) amino acid sequence from Mus musculus |
| REGION | 321..327<br>note = MISC_FEATURE - 3G5 kappa light (Vk) chain CDR2 amino acid sequence from Musmusculus |
| REGION | 360..368<br>note = MISC_FEATURE - 3G5 kappa light (Vk) chain CDR3 amino acid sequence from Musmusculus |
| SITE | 384<br>note = MISC_FEATURE - End of 3G5 kappa light (Vk) chain from Mus musculus |
| REGION | 385..399<br>note = MISC_FEATURE - (GGGGS)3 peptide linker sequence |
| REGION | 400..522<br>note = MISC_FEATURE - anti-MDM monoclonal antibody 3G5 variable heavy (VH) chainpolypeptide sequence from Mus musculus |
| SITE | 400<br>note = MISC_FEATURE - Start of 3G5 variable heavy (VH) chain from Mus musculus |
| REGION | 430..434<br>note = MISC_FEATURE - 3G5 variable heavy (VH) chain CDR1 amino acid sequence from Musmusculus |
| REGION | 449..467<br>note = MISC_FEATURE - 3G5 variable heavy (VH) chain CDR2 amino acid sequence from Musmusculus |
| REGION | 500..511<br>note = MISC_FEATURE - 3G5 variable heavy (VH) chain CDR3 amino acid sequence from Musmusculus |
| SITE | 522<br>note = MISC_FEATURE - End of 3G5 variable heavy (VH) chain from Mus musculus |
| source | 1..522<br>mol_type = protein<br>organism = synthetic construct |

SEQUENCE: 3

```
AGIHDIVLTQ SPASLAVSLG QRATISCRAS KSVSTSSYSY MHWYQQKPGQ PPKLLIKYAS   60
YLESGVPARF SGSGSGTDFT LNIHPVEEED AATYYCQHSR EFPWTFGGGT KLEIKRADAA  120
PGGGGSGGGG SGGGGSEVQL VESGGGLVKP GGSRKLSCAA SGFTFSNYGM HWVRQAPEKG  180
LEWVAYISSG SSTIYYADTV KGRFTISRDN AKNTLFLQMT SLRSEDTAMY YCARRGLLLD  240
YWGQGTTLTV SSASTKGPSV FPLAPLESSG SDIQMTQSPA SLSVSVGETV TITCRASENI  300
YSNLAWYQQK QGKSPQLLVY GATNLADGVP SRFSGSGSGT QYSLKINSLQ SEDFGSYYCQ  360
HFWGTPPTFG GGTKLELKRA DAAPGGGGSG GGGSGGGGSE VQLVESGGGL VQPKGSLKLS  420
CAASGFTFNT YGMNWVRQAP GKGLEWVGRI RTKNNIYATY YDASVKDRFT ISRDDSESML  480
YLQMNNLKTE DTAMYYCVRQ GDELRGYALD YWGQGTSVTV SS                   522
```

|  |  |
|---|---|
| SEQ ID NO: 4<br>FEATURE<br>source | moltype = DNA   length = 12<br>Location/Qualifiers<br>1..12<br>mol_type = other DNA<br>organism = Mus musculus |
| CDS | 1..12<br>note = anti-DNA monoclonal antibody 3E10 kappa light (Vk) chaincomplementarity determining region 1 (CDR1) coding sequence |

SEQUENCE: 4
agttacatgc ac                                                                12

|  |  |
|---|---|
| SEQ ID NO: 5<br>FEATURE<br>source | moltype = AA   length = 4<br>Location/Qualifiers<br>1..4<br>mol_type = protein<br>organism = Mus musculus |

SEQUENCE: 5
SYMH                                                                          4

|  |  |
|---|---|
| SEQ ID NO: 6<br>FEATURE<br>source | moltype = DNA   length = 18<br>Location/Qualifiers<br>1..18 |

|   |   |
|---|---|
|   | mol_type = other DNA<br>organism = Mus musculus |
| CDS | 1..18<br>note = anti-DNA monoclonal antibody 3E10 kappa light (Vk)<br> chaincomplementarity determining region 2 (CDR2) coding<br> sequence |

SEQUENCE: 6
gcatcctacc tagaatct                                                  18

|   |   |
|---|---|
| SEQ ID NO: 7<br>FEATURE<br>source | moltype = AA  length = 6<br>Location/Qualifiers<br>1..6<br>mol_type = protein<br>organism = Mus musculus |

SEQUENCE: 7
ASYLES                                                               6

|   |   |
|---|---|
| SEQ ID NO: 8<br>FEATURE<br>source | moltype = DNA  length = 27<br>Location/Qualifiers<br>1..27<br>mol_type = other DNA<br>organism = Mus musculus |
| CDS | 1..27<br>note = anti-DNA monoclonal antibody 3E10 kappa light (Vk)<br> chaincomplementarity determining region 3 (CDR3) coding<br> sequence |

SEQUENCE: 8
cagcacagta gggagtttcc gtggacg                                        27

|   |   |
|---|---|
| SEQ ID NO: 9<br>FEATURE<br>source | moltype = AA  length = 9<br>Location/Qualifiers<br>1..9<br>mol_type = protein<br>organism = Mus musculus |

SEQUENCE: 9
QHSREFPWT                                                            9

|   |   |
|---|---|
| SEQ ID NO: 10<br>FEATURE<br>source | moltype = DNA  length = 15<br>Location/Qualifiers<br>1..15<br>mol_type = other DNA<br>organism = Mus musculus |
| CDS | 1..15<br>note = anti-DNA monoclonal antibody 3E10 variable heavy<br> (VH) chaincomplementarity determining region 1 (CDR1)<br> coding sequence withD31N mutation at the first amino acid<br> position of CDR1 forenhanced cell penetration |

SEQUENCE: 10
aactatggaa tgcac                                                     15

|   |   |
|---|---|
| SEQ ID NO: 11<br>FEATURE<br>source | moltype = AA  length = 5<br>Location/Qualifiers<br>1..5<br>mol_type = protein<br>organism = Mus musculus |

SEQUENCE: 11
NYGMH                                                                5

|   |   |
|---|---|
| SEQ ID NO: 12<br>FEATURE<br>source | moltype = DNA  length = 51<br>Location/Qualifiers<br>1..51<br>mol_type = other DNA<br>organism = Mus musculus |
| CDS | 1..51<br>note = anti-DNA monoclonal antibody 3E10 variable heavy<br> (VH) chaincomplementarity determining region 2 (CDR2)<br> coding sequence |

SEQUENCE: 12
tacattagta gtggcagtag taccatctac tatgcagaca cagtgaaggg c             51

|   |   |
|---|---|
| SEQ ID NO: 13<br>FEATURE<br>source | moltype = AA  length = 17<br>Location/Qualifiers<br>1..17<br>mol_type = protein<br>organism = Mus musculus |

SEQUENCE: 13
YISSGSSTIY YADTVKG                                                   17

|   |   |
|---|---|
| SEQ ID NO: 14 | moltype = DNA  length = 21 |

```
FEATURE                 Location/Qualifiers
source                  1..21
                        mol_type = other DNA
                        organism = Mus musculus
CDS                     1..21
                        note = anti-DNA monoclonal antibody 3E10 variable heavy
                         (VH) chaincomplementarity determining region 3 (CDR3)
                         coding sequence
SEQUENCE: 14
cgggggttac tacttgacta c                                                   21

SEQ ID NO: 15           moltype = AA  length = 7
FEATURE                 Location/Qualifiers
source                  1..7
                        mol_type = protein
                        organism = Mus musculus
SEQUENCE: 15
RGLLLDY                                                                    7

SEQ ID NO: 16           moltype = DNA  length = 33
FEATURE                 Location/Qualifiers
source                  1..33
                        mol_type = other DNA
                        organism = Mus musculus
CDS                     1..33
                        note = anti-MDM2 monoclonal antibody 3G5 kappa light (Vk)
                         chaincomplementarity determining region 1 (CDR1) coding
                         sequence
SEQUENCE: 16
cgagcaagtg agaatattta cagtaattta gca                                      33

SEQ ID NO: 17           moltype = AA  length = 11
FEATURE                 Location/Qualifiers
source                  1..11
                        mol_type = protein
                        organism = Mus musculus
SEQUENCE: 17
RASENIYSNL A                                                              11

SEQ ID NO: 18           moltype = DNA  length = 21
FEATURE                 Location/Qualifiers
source                  1..21
                        mol_type = other DNA
                        organism = Mus musculus
CDS                     1..21
                        note = anti-MDM2 monoclonal antibody 3G5 kappa light (Vk)
                         chaincomplementarity determining region 2 (CDR2) coding
                         sequence
SEQUENCE: 18
ggtgcaacaa acttagcaga t                                                   21

SEQ ID NO: 19           moltype = AA  length = 7
FEATURE                 Location/Qualifiers
source                  1..7
                        mol_type = protein
                        organism = Mus musculus
SEQUENCE: 19
GATNLAD                                                                    7

SEQ ID NO: 20           moltype = DNA  length = 27
FEATURE                 Location/Qualifiers
source                  1..27
                        mol_type = other DNA
                        organism = Mus musculus
CDS                     1..27
                        note = anti-MDM2 monoclonal antibody 3G5 kappa light (Vk)
                         chaincomplementarity determining region 3 (CDR3) coding
                         sequence
SEQUENCE: 20
caacattttt ggggtactcc tccgacg                                             27

SEQ ID NO: 21           moltype = AA  length = 9
FEATURE                 Location/Qualifiers
source                  1..9
                        mol_type = protein
                        organism = Mus musculus
SEQUENCE: 21
QHFWGTPPT                                                                  9
```

```
SEQ ID NO: 22            moltype = DNA  length = 15
FEATURE                  Location/Qualifiers
source                   1..15
                         mol_type = other DNA
                         organism = Mus musculus
CDS                      1..15
                         note = anti-MDM2 monoclonal antibody 3G5 variable heavy
                          (VH) chaincomplementarity determining region 1 (CDR1)
                          coding sequence
SEQUENCE: 22
acctacggca tgaac                                                          15

SEQ ID NO: 23            moltype = AA  length = 5
FEATURE                  Location/Qualifiers
source                   1..5
                         mol_type = protein
                         organism = Mus musculus
SEQUENCE: 23
TYGMN                                                                      5

SEQ ID NO: 24            moltype = DNA  length = 57
FEATURE                  Location/Qualifiers
source                   1..57
                         mol_type = other DNA
                         organism = Mus musculus
CDS                      1..57
                         note = anti-MDM2 monoclonal antibody 3G5 variable heavy
                          (VH) chaincomplementarity determining region 2 (CDR2)
                          coding sequence
SEQUENCE: 24
cgcataagaa ctaaaaataa tatttatgca acatattatg acgcttcagt gaaagac            57

SEQ ID NO: 25            moltype = AA  length = 19
FEATURE                  Location/Qualifiers
source                   1..19
                         mol_type = protein
                         organism = Mus musculus
SEQUENCE: 25
RIRTKNNIYA TYYDASVKD                                                      19

SEQ ID NO: 26            moltype = DNA  length = 36
FEATURE                  Location/Qualifiers
source                   1..36
                         mol_type = other DNA
                         organism = Mus musculus
CDS                      1..36
                         note = anti-MDM2 monoclonal antibody 3G5 variable heavy
                          (VH) chaincomplementarity determining region 3 (CDR3)
                          coding sequence
SEQUENCE: 26
caaggggacg aattacgagg ttatgctctg gactac                                   36

SEQ ID NO: 27            moltype = AA  length = 12
FEATURE                  Location/Qualifiers
source                   1..12
                         mol_type = protein
                         organism = Mus musculus
SEQUENCE: 27
QGDELRGYAL DY                                                             12

SEQ ID NO: 28            moltype = DNA  length = 1899
FEATURE                  Location/Qualifiers
misc_feature             1..1899
                         note = Coding sequences for full length unprocessed
                          bispecific scFv3E10-PAb421 chimeric antibody derived from
                          Mus musculus, Homosapiens, Saccharomyces cerevisiae, and
                          synthetic sequence from noknown organism
misc_feature             1..3
                         note = ATG, start site of translation provided by
                          pPicZalpha Aexpression vector
misc_feature             1..267
                         note = Saccharomyces cerevisiae-factor secretory signal
                          codingsequence for secretion of fusion protein, provided
                          by pPicZalphaA expression vector
misc_feature             253..258
                         note = Kex2 signal cleavage site between Arg-Glu encoded by
                          nucleotidepositions 253-258 for removing alpha-factor
                          secretory signal
misc_feature             259..264
```

| | |
|---|---|
| | note = Ste13 signal cleavage site between Ala-Glu encoded by nucleotidepositions 259-264 for removingalpha-factor secretory signal |
| misc_feature | 265..270 |
| | note = Ste13 signal cleavage site between Ala-Ala encoded by nucleotidepositions 265-270 for removing alpha-factor secretory signal |
| misc_feature | 268..279 |
| | note = Ala-Gly-Ile-His peptide coding sequence for increasing solubilityof scFv bispecific antibody |
| misc_feature | 272..277 |
| | note = EcoRI restriction enzyme site, recreated after insertion of3E10-PAb421 scFVc EcoRI-XbaI cDNA fragment into EcoRI-XbaI sitesof pPicZ A expression vector |
| misc_feature | 280..1827 |
| | note = 3E10-PAb421 bispecific scFv antibody coding sequence withenhanced cell penetration mutation |
| misc_feature | 280..1023 |
| | note = 3E10 Fv fragment coding sequence with enhanced cell penetrationmutation |
| misc_feature | 280..630 |
| | note = anti-DNA monoclonal antibody 3E10 kappa light (Vk) chain codingsequence from Mus musculus |
| misc_feature | 382..393 |
| | note = 3E10 kappa light (Vk) chain complementarity determining region 1(CDR1) coding sequence from Mus musculus |
| misc_feature | 442..459 |
| | note = 3E10 kappa light (Vk) chain CDR2 coding sequence from Musmusculus |
| misc_feature | 556..582 |
| | note = 3E10 kappa light (Vk) chain CDR3 coding sequence from Musmusculus |
| misc_feature | 631..675 |
| | note = (GGGGS)3 peptide linker coding sequence |
| misc_feature | 766..780 |
| | note = 3E10 variable heavy (VH) chain CDR1 coding sequence from Musmusculus with D31N mutation for enhanced cell penetration |
| misc_feature | 766..768 |
| | note = Asn amino acid coding sequence; D31N mutation in the first aminoacid of CDR1 of 3E10 variable heavy for enhanced cell penetration(VH) chain |
| misc_feature | 823..873 |
| | note = 3E10 variable heavy (VH) chain CDR2 coding sequence from Musmusculus |
| misc_feature | 970..990 |
| | note = 3E10 variable heavy (VH) chain CDR3 coding sequence from Musmusculus |
| misc_feature | 1024..1062 |
| | note = Human constant heavy chain 1 (CH1) linker coding sequence |
| misc_feature | 1063..1080 |
| | note = Swivel coding sequence |
| misc_feature | 1081..1827 |
| | note = PAb421 Fv fragment coding sequence |
| misc_feature | 1081..1434 |
| | note = anti-p53 monoclonal antibody PAb421 kappa light (Vk) chain codingsequence from Mus musculus |
| misc_feature | 1150..1197 |
| | note = PAb421 kappa light (Vk) chain complementarity determining region1 (CDR1) coding sequence from Mus musculus |
| misc_feature | 1243..1263 |
| | note = PAb421 kappa light (Vk) chain complementarity determining region2 (CDR2) coding sequence from Mus musculus |
| misc_feature | 1360..1386 |
| | note = PAb421 kappa light (Vk) chain complementarity determining region3 (CDR3) coding sequence from Mus musculus |
| misc_feature | 1435..1479 |
| | note = (GGGGS)3 peptide linker coding sequence |
| misc_feature | 1480..1827 |
| | note = anti-p53 monoclonal antibody PAb421 variable heavy (VH) chaincoding sequence from Mus musculus |
| misc_feature | 1570..1584 |
| | note = PAb421 variable heavy (VH) chain complementarity determiningregion 1 (CDR1) coding sequence from Mus musculus |

| | | |
|---|---|---|
| misc_feature | 1627..1677 | |
| | note = PAb421 variable heavy (VH) chain complementarity determiningregion 2 (CDR2) coding sequence from Mus musculus | |
| misc_feature | 1774..1794 | |
| | note = PAb421 variable heavy (VH) chain complementarity determiningregion 3 (CDR3) coding sequence from Mus musculus | |
| misc_feature | 1830..1835 | |
| | note = XbaI restriction enzyme site, recreated after insertion of3E10-PAb421 scFVc EcoRI-XbaI cDNA fragment into EcoRI-XbaI sitesof pPicZalpha A expression vector | |
| misc_feature | 1834..1863 | |
| | note = Myc epitope tag, EQKLISEEDL, coding sequence provided bypPicZalpha A expression vector | |
| misc_feature | 1879..1896 | |
| | note = (His)6 epitope tag coding sequence, provided by pPicZalpha Aexpression vector | |
| misc_feature | 1897..1899 | |
| | note = TGA, stop codon provided by pPicZ A expression vector | |
| source | 1..1899 | |
| | mol_type = other DNA | |
| | organism = synthetic construct | |
| CDS | 1..1899 | |
| | note = Coding sequences for full length unprocessed bispecific scFv3E10-PAb421 chimeric antibody with secretory signal, proteasecleavage sites, solubility enhancing peptide and epitope tagsproduced using pPicZalpha A expression vector in Pichia pastoris | |

SEQUENCE: 28

```
atgagatttc cttcaattttt tactgctgtt ttattcgcag catcctccgc attagctgct   60
ccagtcaaca ctacaacaga agatgaaacg gcacaaattc cggctgaagc tgtcatcggt  120
tactcagatt tagaagggga tttcgatgtt gctgttttgc cattttccaa cagcacaaat  180
aacgggttat tgtttataaa tactactatt gccagcattg ctgctaaaga agaagggta   240
tctctcgaga aaagagaggc tgaagctgca ggaattcacg acattgtcct gacacagtct  300
cctgcttcct tagctgtatc tctggggcag agggccacca tctcctgcag ggccagcaaa  360
agtgtcagta catctagcta tagttacatg cactggtacc aacagaaacc aggacagcca  420
cccaaactcc tcatcaagta tgcatcctac ctagaatctg gggttcctgc caggttcagt  480
ggcagtgggt ctgggacaga cttcacctc aatcatcatc ctgtgaggga gaggatgct   540
gcaacatatt actgtcagca cagtagggag tttccgtgga cgttcggtgg aggcaccaag  600
ctggaaatca acggctgag ctgcacccc ggggtggcg ttctggcgg tggcggttct    660
ggaggcggtg gctctgaggt gcagctggtg gagtctgggg gaggcttagt gaagcctgga  720
gggtcccgga aactctcctg tgcagcctct ggattcactt tcagtaacta tggaatgcac  780
tgggtccgtc aggctccaga aaggggctg gagtgggttg catacattag tagtggcagt  840
agtaccatct actatgcaga cacagtgaag ggccgattca ccatctccag agacaatgcc  900
aagaacaccc tgttcctgca aatgaccagt ctaaggtctg aggacacagc catgtattac  960
tgtcgcaaggc ggggggttact acttgactac tggggccaag gcaccactct cacagtctcc 1020
tcagcttcca ccaagggccc atccgtcttc cccctggcgc cctggagtc ttccggatcc   1080
gatgttgtga tgacccagac tccactcact ttgtcggtta ccattggaca accagcctcc  1140
atctcttgca agtcaagtca gagcctcttg gatagtgatg gaaagacata cttgaattgg  1200
ttgttacaga ggccaggcca gtctccaaag cgcctaatct atctggtgtc taaactggac  1260
tctggagtcc ctgacaggtt cactggcagt ggatcaggga cagatttcac actgaaaatc  1320
aacagagtgg aggctgagga tttgggagtt tattattgct ggcaaggtac acattctccg  1380
ctcacgttcg gtgctggcac caagctgaa attaaacggg ctgacgctgc acccggggga  1440
ggggatctg gtggcggcgg atcaggtgga ggtgatctc aggtgcagct gcagcagtct  1500
ggggcagagc ttgtgaggtc aggggcctca gtcaagttgt cctgcacagc ttctggcttc  1560
aacattaaag actactatat gcactgggtg aagcagaggc ctgaacaggg cctgagtgg   1620
attggatgga ttgatcctga aaatggtgat actgaatatg ccccgaagtt ccagggcaag  1680
gccactatga ctgcagacac atcctccgat acagcctacc tgcagctcag cagcctggca  1740
tctgaggaca ctgccgtcta ttattgtaat tttttacgggg atgctttgga ctactggggt  1800
caaggaacct cggtcaccgt ctcctctcat ttagaacaaa aactcatctc agaagaggat  1860
ctgaatagcg ccgtcgacca tcatcatcat catcattga                         1899
```

| | | |
|---|---|---|
| SEQ ID NO: 29 | moltype = AA   length = 632 | |
| FEATURE | Location/Qualifiers | |
| REGION | 1..632 | |
| | note = Synthetic Construct | |
| source | 1..632 | |
| | mol_type = protein | |
| | organism = synthetic construct | |

SEQUENCE: 29

```
MRFPSIFTAV LFAASSALAA PVNTTTEDET AQIPAEAVIG YSDLEGDFDV AVLPFSNSTN   60
NGLLFINTTI ASIAAKEEGV SLEKREAEAA GIHDIVLTQS PASLAVSLGQ RATISCRASK  120
SVSTSSYSYM HWYQQKPGQP PKLLIKYASY LESGVPARFS GSGSGTDFTL NIHPVEEEDA  180
ATYYCQHSRE FPWTFGGGTK LEIKRADAAP GGGGSGGGGS GGGGSEVQLV ESGGGLVKPG  240
GSRKLSCAAS GFTFSNYGMH WVRQAPEKGL EWVAYISSGS STIYYADTVK GRFTISRDNA  300
KNTLFLQMTS LRSEDTAMYY CARRGLLLDY WGQGTTLTVS SASTKGPSVF PLAPLESSGS  360
DVVMTQTPLT LSVTIGQPAS ISCKSSQSLL DSDGKTYLNW LLQRPGQSPK RLIYLVSKLD  420
SGVPDRFTGS GSGTDFTLKI NRVEAEDLGV YYCWQGTHSP LTFGAGTKLE IKRADAAPGG  480
```

```
GGSGGGGSGG GGSQVQLQQS GAELVRSGAS VKLSCTASGF NIKDYYMHWV KQRPEQGLEW   540
IGWIDPENGD TEYAPKFQGK ATMTADTSSD TAYLQLSSLA SEDTAVYYCN FYGDALDYWG   600
QGTSVTVSSH LEQKLISEED LNSAVDHHHH HH                                 632
```

| SEQ ID NO: 30 | moltype = AA  length = 520 |
|---|---|
| FEATURE | Location/Qualifiers |
| REGION | 1..520 |
| | note = Protein sequence for bispecific scFv 3E10-PAb421 chimericantibody derived from Mus musculus, Homo sapiens, and syntheticsequence from no known organism with increased solubility peptidebut without signal sequence or epitope tag. |
| REGION | 1..4 |
| | note = MISC_FEATURE - AGIH peptide for increased solubility |
| REGION | 5..520 |
| | note = MISC_FEATURE - 3E10-PAb4215 bispecific scFv chimeric antibody with enhanced cellpenetration mutation but no secretory signal or epitope tag |
| SITE | 5 |
| | note = MISC_FEATURE - Start of 3E10 kappa light (Vk) chain from Mus musculus |
| REGION | 5..252 |
| | note = MISC_FEATURE - 3E10 Fv fragment with enhanced cell penetration mutation (D31Nmutation at CDR1 of 3E10 VH chain) |
| REGION | 5..121 |
| | note = MISC_FEATURE - anti-DNA monoclonal antibody 3E10 kappa light (Vk) chainpolypeptide sequence from Mus musculus |
| REGION | 39..42 |
| | note = MISC_FEATURE - 3E10 kappa light (Vk) chain complementarity determining region 1(CDR1) amino acid sequence from Mus musculus |
| REGION | 59..64 |
| | note = MISC_FEATURE - 3E10 kappa light (Vk) chain CDR2 amino acid sequence from Musmusculus |
| REGION | 97..105 |
| | note = MISC_FEATURE - 3E10 kappa light (Vk) chain CDR3 amino acid sequence from Musmusculus |
| SITE | 121 |
| | note = MISC_FEATURE - End of 3E10 kappa light (Vk) chain from Mus musculus |
| REGION | 122..136 |
| | note = MISC_FEATURE - (GGGGS)3 peptide linker sequence |
| REGION | 137..252 |
| | note = MISC_FEATURE - anti-DNA monoclonal antibody 3E10 variable heavy (VH) chainpolypeptide sequence from Mus musculus with enhanced cellpenetration mutation (D31N mutation at CDR1 of 3E10 VH chain) |
| SITE | 137 |
| | note = MISC_FEATURE - Start of 3E10 variable heavy (VH) chain from Mus musculus |
| REGION | 167..171 |
| | note = MISC_FEATURE - 3E10 variable heavy (VH) chain CDR1 amino acid sequence from Musmusculus with D31N mutation for enhanced cell penetration |
| SITE | 167 |
| | note = MISC_FEATURE - Asn amino acid; D31N mutation in first amino acid of CDR1 of 3E10variable heavy (VH) chain for enhanced cell penetration |
| REGION | 186..202 |
| | note = MISC_FEATURE - 3E10 variable heavy (VH) chain CDR2 amino acid sequence from Musmusculus |
| REGION | 235..241 |
| | note = MISC_FEATURE - 3E10 variable heavy (VH) chain CDR3 amino acid sequence from Musmusculus |
| SITE | 252 |
| | note = MISC_FEATURE - End of 3E10 variable heavy (VH) chain from Mus musculus |
| REGION | 253..265 |
| | note = MISC_FEATURE - Human constant heavy chain 1 (CH1) linker sequence |
| REGION | 266..271 |
| | note = MISC_FEATURE - Swivel sequence |
| REGION | 272..520 |
| | note = MISC_FEATURE - PAb421 Fv fragment polypeptide sequence |
| REGION | 272..389 |
| | note = MISC_FEATURE - anti-p53 monoclonal antibody PAb421 |

|  |  |
|---|---|
| | kappa light (Vk) chainpolypeptide sequence from Mus musculus |
| SITE | 272 |
| | note = MISC_FEATURE - Start of PAb421 kappa light (Vk) chain from Mus musculus |
| REGION | 295..310 |
| | note = MISC_FEATURE - PAb421 kappa light (Vk) chain complementarity determining region1 (CDR1) amino acid sequence from Mus musculus |
| REGION | 326..332 |
| | note = MISC_FEATURE - PAb421 kappa light (Vk) chain CDR2 amino acid sequence from Musmusculus |
| REGION | 365..373 |
| | note = MISC_FEATURE - PAb421 kappa light (Vk) chain CDR3 amino acid sequence from Musmusculus |
| SITE | 389 |
| | note = MISC_FEATURE - End of PAb421 kappa light (Vk) chain from Mus musculus |
| REGION | 390..404 |
| | note = MISC_FEATURE - (GGGGS)3 peptide linker sequence |
| REGION | 405..520 |
| | note = MISC_FEATURE - anti-p53 monoclonal antibody PAb421 variable heavy (VH) chainpolypeptide sequence from Mus musculus |
| SITE | 405 |
| | note = MISC_FEATURE - Start of PAb421 variable heavy (VH) chain from Mus musculus |
| REGION | 435..439 |
| | note = MISC_FEATURE - PAb421 variable heavy (VH) chain CDR1 amino acid sequence fromMus musculus |
| REGION | 454..470 |
| | note = MISC_FEATURE - PAb421 variable heavy (VH) chain CDR2 amino acid sequence fromMus musculus |
| REGION | 503..509 |
| | note = MISC_FEATURE - PAb421 variable heavy (VH) chain CDR3 amino acid sequence fromMus musculus |
| SITE | 520 |
| | note = MISC_FEATURE - End of PAb421 variable heavy (VH) chain from Mus musculus |
| source | 1..520 |
| | mol_type = protein |
| | organism = synthetic construct |

SEQUENCE: 30
```
AGIHDIVLTQ SPASLAVSLG QRATISCRAS KSVSTSSYSY MHWYQQKPGQ PPKLLIKYAS    60
YLESGVPARF SGSGSGTDFT LNIHPVEEED AATYYCQHSR EFPWTFGGGT KLEIKRADAA   120
PGGGGSGGGG SGGGGSEVQL VESGGGLVKP GGSRKLSCAA SGFTFSNYGM HWVRQAPEKG   180
LEWVAYISSG SSTIYYADTV KGRFTISRDN AKNTLFLQMT SLRSEDTAMY YCARRGLLLD   240
YWGQGTTLTV SSASTKGPSV FPLAPLESSG SDVVMTQTPL TLSVTIGQPA SISCKSSQSL   300
LDSDGKTYLN WLLQRPGQSP KRLIYLVSKL DSGVPDRFTG SGSGTDFTLK INRVEAEDLG   360
VYYCWQGTHS PLTFGAGTKL EIKRADAAPG GGGSGGGGS GGGGSQVQLQQ SGAELVRSGA   420
SVKLSCTASG FNIKDYYMHW VKQRPEQGLE WIGWIDPENG DTEYAPKFQG KATMTADTSS   480
DTAYLQLSSL ASEDTAVYYC NFYGDALDYW GQGTSVTVSS                        520
```

|  |  |
|---|---|
| SEQ ID NO: 31 | moltype = DNA length = 48 |
| FEATURE | Location/Qualifiers |
| source | 1..48 |
| | mol_type = other DNA |
| | organism = Mus musculus |
| CDS | 1..48 |
| | note = anti-p53 monoclonal antibody PAb421 kappa light (Vk) chaincomplementarity determining region 1 (CDR1) amino acid sequencefrom Mus musculus |

SEQUENCE: 31
```
aagtcaagtc agagcctctt ggatagtgat ggaaagacat acttgaat              48
```

|  |  |
|---|---|
| SEQ ID NO: 32 | moltype = AA length = 16 |
| FEATURE | Location/Qualifiers |
| source | 1..16 |
| | mol_type = protein |
| | organism = Mus musculus |

SEQUENCE: 32
```
KSSQSLLDSD GKTYLN                                                 16
```

|  |  |
|---|---|
| SEQ ID NO: 33 | moltype = DNA length = 21 |
| FEATURE | Location/Qualifiers |
| source | 1..21 |
| | mol_type = other DNA |
| | organism = Mus musculus |
| CDS | 1..21 |

```
                        note = anti-p53 monoclonal antibody PAb421 kappa light (Vk)
                           chaincomplementarity determining region 2 (CDR2) amino
                           acid sequencefrom Mus musculus
SEQUENCE: 33
ctggtgtcta aactggactc t                                              21

SEQ ID NO: 34           moltype = AA  length = 7
FEATURE                 Location/Qualifiers
source                  1..7
                        mol_type = protein
                        organism = Mus musculus
SEQUENCE: 34
LVSKLDS                                                              7

SEQ ID NO: 35           moltype = DNA  length = 27
FEATURE                 Location/Qualifiers
source                  1..27
                        mol_type = other DNA
                        organism = Mus musculus
CDS                     1..27
                        note = anti-p53 monoclonal antibody PAb421 kappa light (Vk)
                           chaincomplementarity determining region 3 (CDR3) amino
                           acid sequencefrom Mus musculus
SEQUENCE: 35
tggcaaggta cacattctcc gctcacg                                        27

SEQ ID NO: 36           moltype = AA  length = 9
FEATURE                 Location/Qualifiers
source                  1..9
                        mol_type = protein
                        organism = Mus musculus
SEQUENCE: 36
WQGTHSPLT                                                            9

SEQ ID NO: 37           moltype = DNA  length = 15
FEATURE                 Location/Qualifiers
source                  1..15
                        mol_type = other DNA
                        organism = Mus musculus
CDS                     1..15
                        note = anti-p53 monoclonal antibody PAb421 variable heavy
                           (VH) chaincomplementarity determining region 1 (CDR1)
                           coding sequence
SEQUENCE: 37
gactactata tgcac                                                     15

SEQ ID NO: 38           moltype = AA  length = 5
FEATURE                 Location/Qualifiers
source                  1..5
                        mol_type = protein
                        organism = Mus musculus
SEQUENCE: 38
DYYMH                                                                5

SEQ ID NO: 39           moltype = DNA  length = 51
FEATURE                 Location/Qualifiers
source                  1..51
                        mol_type = other DNA
                        organism = Mus musculus
CDS                     1..51
                        note = anti-p53 monoclonal antibody PAb421 variable heavy
                           (VH) chaincomplementarity determining region 2 (CDR2)
                           coding sequence
SEQUENCE: 39
tggattgatc ctgagaatgg tgatactgaa tatgccccga agttccaggg c              51

SEQ ID NO: 40           moltype = AA  length = 17
FEATURE                 Location/Qualifiers
source                  1..17
                        mol_type = protein
                        organism = Mus musculus
SEQUENCE: 40
WIDPENGDTE YAPKFQG                                                   17

SEQ ID NO: 41           moltype = DNA  length = 21
FEATURE                 Location/Qualifiers
source                  1..21
                        mol_type = other DNA
                        organism = Mus musculus
```

-continued

```
CDS                     1..21
                        note = anti-p53 monoclonal antibody PAb421 variable heavy
                        (VH) chaincomplementarity determining region 3 (CDR3)
                        coding sequence
SEQUENCE: 41
tacggggatg ctttggacta c                                              21

SEQ ID NO: 42           moltype = AA  length = 7
FEATURE                 Location/Qualifiers
source                  1..7
                        mol_type = protein
                        organism = Mus musculus
SEQUENCE: 42
YGDALDY                                                               7
```

What is claimed is:

1. A bispecific antibody comprising the amino acid sequence of SEQ ID NO: 29 or 30.

2. The bispecific antibody of claim 1, wherein the bispecific antibody is a chimeric antibody, or a humanized antibody.

3. A pharmaceutical composition comprising the bispecific antibody of claim 1.

4. The pharmaceutical composition of claim 3, further comprising a pharmaceutically acceptable carrier.

5. The bispecific antibody of claim 1, wherein the bispecific antibody is conjugated to a chemotherapeutic agent, a toxin, a radioisotope, or a detectable label.

* * * * *